(12) United States Patent
Aihara et al.

(10) Patent No.: US 8,674,091 B2
(45) Date of Patent: Mar. 18, 2014

(54) 1,3,5-TRIAZINE DERIVATIVE, PROCESS FOR PRODUCING SAME, AND ORGANIC ELECTROLUMINESCENT ELEMENT COMPRISING SAME AS CONSTITUENT

(75) Inventors: Hidenori Aihara, Ayase (JP); Yousuke Hisamatsu, Ayase (JP); Tsuyoshi Tanaka, Ayase (JP); Yuichi Miyashita, Ayase (JP); Nobumichi Arai, Ayase (JP); Naoki Uchida, Ayase (JP); Takashi Iida, Ayase (JP)

(73) Assignees: Tosoh Corporation, Yamacuchi (JP); Sagami Chemical Research Institute, Kanagawa (JP)

( * ) Notice: Subject to any disclaimer, the term of this patent is extended or adjusted under 35 U.S.C. 154(b) by 120 days.

(21) Appl. No.: 13/131,972

(22) PCT Filed: Dec. 1, 2009

(86) PCT No.: PCT/JP2009/070170
§ 371 (c)(1),
(2), (4) Date: Aug. 12, 2011

(87) PCT Pub. No.: WO2010/064627
PCT Pub. Date: Jun. 10, 2010

(65) Prior Publication Data
US 2011/0288295 A1    Nov. 24, 2011

(30) Foreign Application Priority Data
Dec. 1, 2008  (JP) ................................. 2008-306303

(51) Int. Cl.
| | |
|---|---|
| C07D 251/24 | (2006.01) |
| C07D 401/04 | (2006.01) |
| C07D 401/14 | (2006.01) |
| C07D 403/04 | (2006.01) |
| C07D 403/14 | (2006.01) |
| C09K 11/06 | (2006.01) |
| C07B 61/00 | (2006.01) |
| H01L 51/50 | (2006.01) |

(52) U.S. Cl.
USPC ................................. 544/180; 345/82; 345/76

(58) Field of Classification Search
USPC ........................................ 544/180; 345/82, 76
See application file for complete search history.

(56) References Cited

U.S. PATENT DOCUMENTS

| | | | |
|---|---|---|---|
| 6,057,048 A | 5/2000 | Hu et al. | |
| 6,225,467 B1 | 5/2001 | Esteghamatian et al. | |
| 6,229,012 B1 | 5/2001 | Hu et al. | |
| 6,656,608 B1 | 12/2003 | Kita et al. | |
| 7,994,316 B2 | 8/2011 | Yamakawa et al. | |
| 8,268,997 B2 * | 9/2012 | Yamakawa et al. | 544/180 |
| 2009/0281311 A1 | 11/2009 | Yamakawa et al. | |
| 2010/0090588 A1 | 4/2010 | Yokoyama et al. | |
| 2010/0249406 A1 | 9/2010 | Yamakawa et al. | |
| 2011/0190494 A1 | 8/2011 | Aihara et al. | |

FOREIGN PATENT DOCUMENTS

| | | |
|---|---|---|
| JP | 7-157473 A | 6/1995 |
| JP | 2001-143869 A | 5/2001 |
| JP | 2003-45662 A | 2/2003 |
| JP | 2003-282270 A | 10/2003 |
| JP | 2003-303689 A | 10/2003 |
| JP | 2004-22334 A | 1/2004 |
| JP | 2004-063465 | 2/2004 |
| JP | 2007-137829 A | 6/2007 |
| JP | 2007-140808 A | 6/2007 |
| JP | 2007-177252 A | 7/2007 |
| JP | 2007-223929 A | 9/2007 |
| JP | 2007-314503 A | 12/2007 |
| JP | 2008-280330 A | 11/2008 |
| WO | 2008/023628 A1 | 2/2008 |
| WO | 2008/129912 | 10/2008 |

OTHER PUBLICATIONS

Christoph Meier et al., "Adsorbate-Substrate-Medicated Growth of Oligopyridine Monolayers at the Solid/Liquid Interface", Journal of Physical Chemistry C. vol. 113, No. 4, (2009). American Chemical Society, Jan. 29, 2009, pp. 1507-1514.
International Search Report received in connection with PCT/JP2009/070170, mail date is Dec. 28, 2009.
Search report from E.P.O. that issued with respect to patent family member European Patent Application No. 09830393.6, mail date is Sep. 20, 2011.

\* cited by examiner

*Primary Examiner* — Venkataraman Balasubramanian
(74) *Attorney, Agent, or Firm* — Greenblum & Bernstein, P.L.C.

(57) ABSTRACT

A 1,3,5-triazine derivative represented by formula (1):

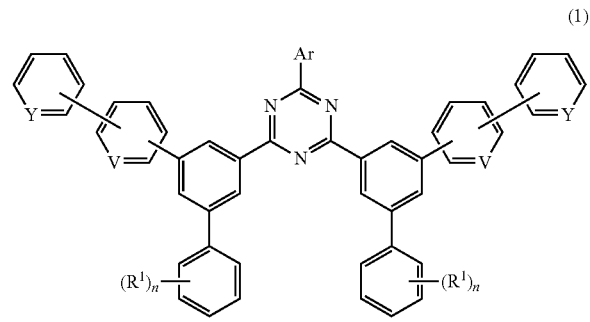

wherein $R^1$ is hydrogen, $C_{1-4}$ alkyl group or substituted or unsubstituted phenyl group; n is an integer of 1-3, Ar is a substituted or unsubstituted aromatic hydrocarbon group, provided that Ar is different from two substituted quarterarylenyl groups bonded to the 1,3,5-triazine ring; and V and Y are nitrogen or carbon, provided that a case where both of V and Y are carbon atoms is excluded. The organic electroluminescent device comprising the 1,3,5-triazine derivative as an electron transport material has a long lifetime.

3 Claims, 1 Drawing Sheet

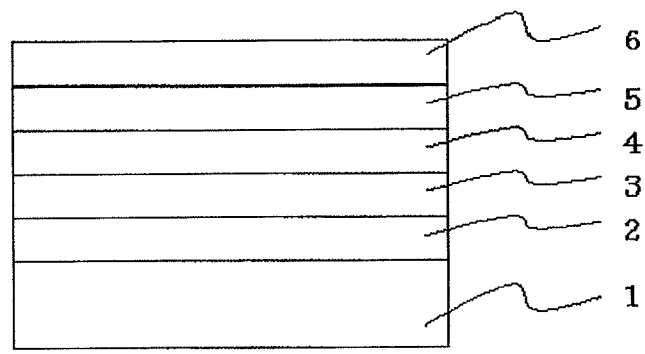

1,3,5-TRIAZINE DERIVATIVE, PROCESS FOR PRODUCING SAME, AND ORGANIC ELECTROLUMINESCENT ELEMENT COMPRISING SAME AS CONSTITUENT

TECHNICAL FIELD

This invention relates to a 1,3,5-triazine derivative having a quarterarylenyl group containing a pyridyl group, which is useful as a constituent of an organic electroluminescent device. The invention further relates to a process for producing the 1,3,5-triazine derivative, and an organic electroluminescent device comprising the 1,3,5-triazine derivative.

The 1,3,5-triazine derivative according to the present invention has good charge transporting characteristics and therefore is suitable as a constituent of an organic electroluminescent device. Thus, the present invention further relates to an organic electroluminescent device comprising the 1,3,5-triazine derivative as at least one layer in the device, which exhibits an improved driving property and an enhanced lifetime.

BACKGROUND ART

An organic electroluminescent device has a multilayer structure comprising (i) a luminescent layer comprising a light emitting compound, (ii) a hole transport layer and an electron transport layer, which sandwich the luminescent layer, and (iii) an anode and a cathode, which sandwich the hole transport layer, the luminescent layer and the electron transport layer. The organic electroluminescent device utilizes light emission (fluorescence or phosphorescence) occurring at deactivation of an exciton formed by the recombination of electron with hole, which are injected in the luminescent layer. Utilizing this feature, the organic electroluminescent device is applied to displays and others.

The 1,3,5-triazine derivative according to the present invention is novel and characterized as having quarterarylenyl groups having a pyridyl group in 2- and 4-positions of the 1,3,5-triazine ring, and an aromatic hydrocarbon group in a 6-position thereof.

Recently, various 1,3,5-triazine derivatives for use in an organic electroluminescent device have been proposed (see, for example, patent documents 1 to 4). These proposed triazine derivatives have 2,4-di-substituted phenyl groups or 3,4-di-substituted phenyl groups in 2-, 4- and 6-positions of a triazine ring, and thus, are distinguished from the 1,3,5-triazine derivative of the present invention, which has quarterarylenyl groups having a pyridyl group in 2- and 4-positions of the 1,3,5-triazine ring.

Further, 1,3,5-triazine derivatives for use in an organic electroluminescent device have been proposed (see, for example, patent documents 5 and 6). These proposed triazine derivatives have substituted phenyl groups in 2-, 4- and 6-positions of a triazine ring, but, the positions in the phenyl groups in which substituents are bonded to the phenyl groups are indefinite. The 1,3,5-triazine derivative of the present invention, which has quarterarylenyl groups having a pyridyl group, in 2- and 4-positions of the 1,3,5-triazine ring, is not described in these patent documents.

A triazine derivative having in the triazine ring quarterarylenyl groups containing pyridyl groups, for use in an organic electroluminescent device, have been proposed (see, for example, patent document 7). The proposed triazine derivative has quaterarylenyl groups, each chain end of which is bonded to the triazine ring of the triazine derivative. Thus, the proposed triazine derivative is distinguished from the 1,3,5-triazine derivative of the present invention, which has quarterarylenyl groups bonded to the 1,3,5-triazine ring in the midway of each quarterarylenyl group.

Still another 1,3,5-triazine derivative for use in an organic electroluminescent device has been proposed (see, for example, patent document 8). The proposed triazine derivative has 3,5-di-substituted phenyl group in a 2-position of the triazine ring, and thus, is distinguished from the 1,3,5-triazine derivative of the present invention,

PRIOR ART PATENT DOCUMENTS

Patent document 1: U.S. Pat. No. 6,057,048
Patent document 2: U.S. Pat. No. 6,229,012
Patent document 3: U.S. Pat. No. 6,225,467
Patent document 4: JP 2004-63465 A
Patent document 5: JP 2004-22334 A
Patent document 6: JP 2007-137829 A
Patent document 7: JP 2007-314503 A
Patent document 8: JP 2008-280330 A

DISCLOSURE OF THE INVENTION

Problems to be Solved by the Invention

An object of the present invention is to provide a 1,3,5-triazine derivative having a novel structure, which gives an organic electroluminescent device operable at a sufficiently reduced driving voltage and having a long lifetime.

Another object of the present invention is to provide a process for producing the above-mentioned 1,3,5-triazine derivative by an industrially advantageous process.

A further object of the present invention is to provide an organic electroluminescent device which is operated at a sufficiently reduced driving voltage and has a long lifetime.

Means for Solving the Problems

The inventors made an extensive research for solving the above-mentioned problems, and found that the 1,3,5-triazine derivative of the present invention can be formed into an amorphous thin film by any conventional procedure including vacuum deposition, and further that an organic electroluminescent device comprising the 1,3,5-triazine derivative as an electron transport layer is operated at a sufficiently reduced driving voltage and has a long lifetime, as compared with the conventional organic electroluminescent devices. On the basis of these findings, the present invention has been completed.

Thus, in one aspect of the present invention, there is provided a 1,3,5-triazine derivative represented by the following general formula (1):

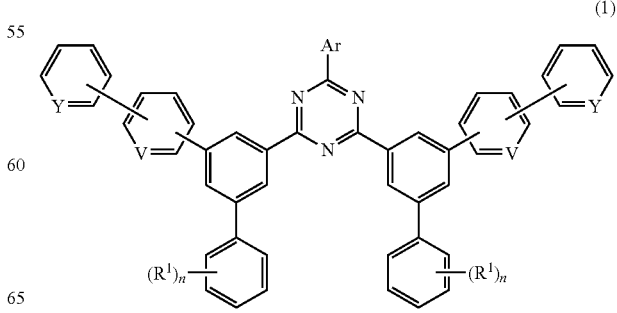

(1)

wherein:

R¹ represents a hydrogen atom, an alkyl group having 1 to 4 carbon atoms, or a substituted or unsubstituted phenyl group; n is an integer of 1 to 3, and, when n is 2 or 3, R¹ may be the same or different;

Ar represents a substituted or unsubstituted aromatic hydrocarbon group, provided that Ar is different from the two substituted quarterarylenyl groups bonded to the 1,3,5-triazine ring in the derivative of the formula (1); and V and Y independently represent a nitrogen atom or a carbon atom, provided that a case where both of V and Y are carbon atoms is excluded.

In another aspect of the present invention, there is provided a process for producing a 1,3,5-triazine derivative represented by the following general formula (1):

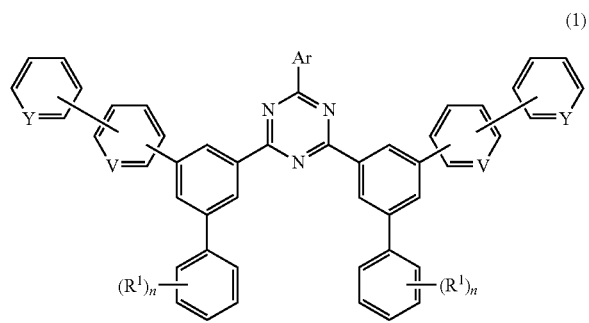

(1)

wherein:

R¹ represents a hydrogen atom, an alkyl group having 1 to 4 carbon atoms, or a substituted or unsubstituted phenyl group; n is an integer of 1 to 3, and, when n is 2 or 3, R¹ may be the same or different;

Ar represents a substituted or unsubstituted aromatic hydrocarbon group, provided that Ar is different from the two substituted quarterarylenyl groups bonded to the 1,3,5-triazine ring in the derivative of the formula (1); and V and Y independently represent a nitrogen atom or a carbon atom, provided that a case where both of V and Y are carbon atoms is excluded;

characterized by coupling a compound represented by the following general formula (2) with a compound represented by the following general formula (3) in the presence of a palladium catalyst and in the presence or absence of a base;

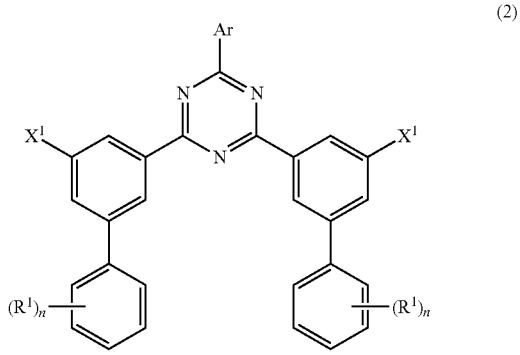

(2)

wherein:

R¹, n and Ar are the same as defined with regard to the formula (1), and

X¹ represents a leaving group;

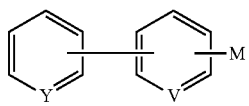

(3)

wherein:

V and Y are the same as defined with regard to the formula (1), and

M represents a metal-containing group or a hetero atom-containing group.

In still another aspect of the present invention, there is provided a process for producing a 1,3,5-triazine derivative represented by the following general formula (1):

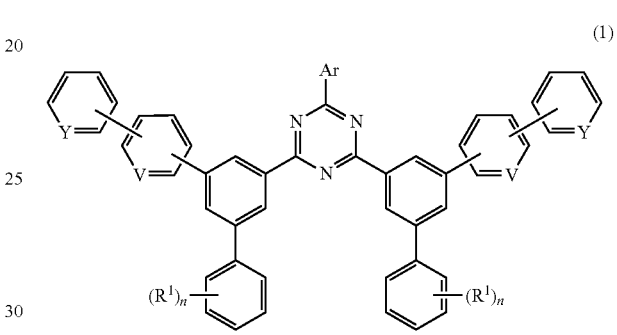

(1)

wherein:

R¹ represents a hydrogen atom, an alkyl group having 1 to 4 carbon atoms, or a substituted or unsubstituted phenyl group; n is an integer of 1 to 3, and, when n is 2 or 3, R¹ may be the same or different;

Ar represents a substituted or unsubstituted aromatic hydrocarbon group, provided that Ar is different from the two substituted quarterarylenyl groups bonded to the 1,3,5-triazine ring in the derivative of the formula (1); and V and Y independently represent a nitrogen atom or a carbon atom, provided that a case where both of V and Y are carbon atoms is excluded;

characterized by coupling a compound represented by the following general formula (4) with a compound represented by the following general formula (5) in the presence of a palladium catalyst and a base;

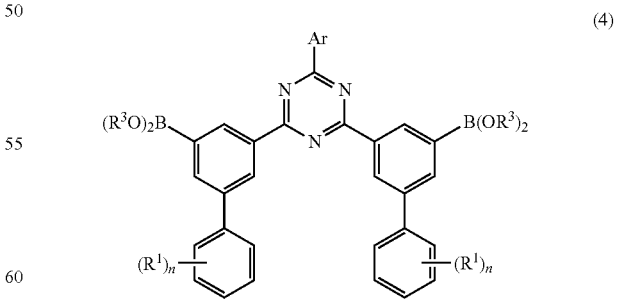

(4)

wherein:

R¹, n and Ar are the same as defined with regard to the formula (1), and the two R³s in —B(OR³)₂ may be the same or different, and each R³ represents a hydrogen atom, an alkyl group having 1 to 4 carbon atoms or a phenyl group, and the two $R^3$s can form a ring together with the two oxygen atoms and the boron atom;

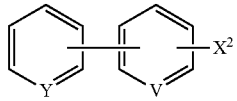

(5)

wherein:

Y and V are the same as defined with regard to the formula (1); and $X^2$ represents a leaving group.

In a further aspect of the present invention, there is provided an organic electroluminescent device characterized by comprising as a constituent a 1,3,5-triazine derivative represented by the following general formula (1):

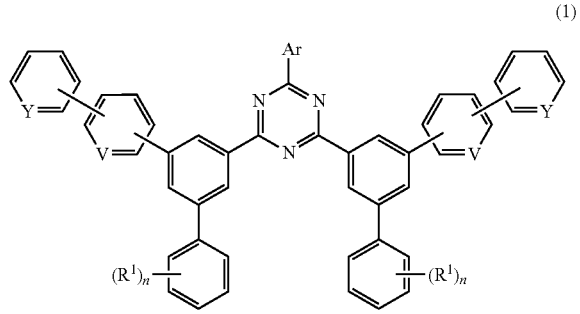

(1)

wherein:

$R^1$ represents a hydrogen atom, an alkyl group having 1 to 4 carbon atoms, or a substituted or unsubstituted phenyl group; n is an integer of 1 to 3, and, when n is 2 or 3, $R^1$ may be the same or different;

Ar represents a substituted or unsubstituted aromatic hydrocarbon group, provided that Ar is different from the two substituted quarterarylenyl groups bonded to the 1,3,5-triazine ring in the derivative of the formula (1); and V and Y independently represent a nitrogen atom or a carbon atom, provided that a case where both of V and Y are carbon atoms is excluded.

Effect of the Invention

A thin film composed of the 1,3,5-triazine derivative of formula (1) according to the present invention has outstanding properties in surface smoothness, amorphousness, heat resistance, electron transportability, hole blocking capability, resistance to oxidation and reduction, moisture resistance, oxygen resistance and electron injection property. Therefore, the thin film is useful as a material for an organic electroluminescent device, especially as a material for, for example, an electron transport layer, a hole blocking layer and a light emitting host layer of an organic electroluminescent device.

Thus, the thin film composed of the 1,3,5-triazine derivative of formula (1) according to the present invention is suitable for an organic electroluminescent device operable at a sufficiently reduced driving voltage and having a long lifetime.

BRIEF DESCRIPTION OF THE DRAWINGS

FIG. 1 illustrates a schematic cross-section of an example of an organic electroluminescent device having a layer composed of a thin film of the 1,3,5-triazine derivative according to the present invention.

EXPLANATION OF REFERENCE NUMERALS

1. Glass substrate with transparent ITO electrode
2. Hole injection layer
3. Hole transport layer
4. Light emitting layer
5. Electron transport layer
6. Cathode layer

MODE FOR CARRYING OUT THE INVENTION

The invention will now be described in detail.

In the general formula (1), $R^1$ represents a hydrogen atom, an alkyl group having 1 to 4 carbon atoms, or a substituted or unsubstituted phenyl group. Of these, a hydrogen atom is preferable in view of the performance as a material for an organic electroluminescent device.

As specific examples of the alkyl group having 1 to 4 carbon atoms, represented by $R^1$ in the general formula (1), there can be mentioned a methyl group, an ethyl group, a propyl group, a 2-propyl group, a butyl group and a tert-butyl group. Of these, a methyl group is preferable in view of ease in synthesis and the performance as a material for an organic electroluminescent device.

As specific examples of the substituted or unsubstituted phenyl group, represented by $R^1$ in the general formula (1), there can be mentioned phenyl group, p-tolyl group, m-tolyl group, o-tolyl group, 4-trifluoromethylphenyl group, 3-trifluoromethylphenyl group, 2-trifluoromethylphenyl group, 2,4-dimethylphenyl group, 3,5-dimethylphenyl group, mesityl group, 2-ethylphenyl group, 3-ethylphenyl group, 4-ethylphenyl group, 2,4-diethylphenyl group, 3,5-diethylphenyl group, 2-propylphenyl group, 3-propylphenyl group, 4-propylphenyl group, 2,4-dipropylphenyl group, 3,5-dipropylphenyl group, 2-isopropylphenyl group, 3-isopropylphenyl group, 4-isopropylphenyl group, 2,4-diisopropylphenyl group, 3,5-diisopropylphenyl group, 2-butylphenyl group, 3-butylphenyl group, 4-butylphenyl group, 2,4-dibutylphenyl group, 3,5-dibutylphenyl group, 2-tert-butylphenyl group, 3-tert-butylphenyl group, 4-tert-butylphenyl group, 2,4-di-tert-butylphenyl group, 3,5-di-tert-butylphenyl group, 4-biphenylyl group, 3-biphenylyl group, 2-biphenylyl group, 2-methylbiphenyl-4-yl group, 3-methylbiphenyl-4-yl group, 2'-methylbiphenyl-4-yl group, 4'-methylbiphenyl-4-yl group, 2,2'-dimethylbiphenyl-4-yl group, 2',4',6'-trimethylbiphenyl-4-yl group, 6-methylbiphenyl-3-yl group, 5-methylbiphenyl-3-yl group, 2'-methylbiphenyl-3-yl group, 4'-methylbiphenyl-3-yl group, 6,2'-dimethylbiphenyl-3-yl group, 2',4',6'-trimethylbiphenyl-3-yl group, 5-methylbiphenyl-2-yl group, 6-methylbiphenyl-2-yl group, 2'-methylbiphenyl-2-yl group, 4'-methylbiphenyl-2-yl group, 6,2'-dimethylbiphenyl-2-yl group, 2',4',6'-trimethylbiphenyl-2-yl group, 2-trifluoromethylbiphenyl-4-yl group, 3-trifluoromethylbiphenyl-4-yl group, 2'-trifluoromethylbiphenyl-4-yl group, 4'-trifluoromethylbiphenyl-4-yl group, 6-trifluoromethylbiphenyl-3-yl group, 5-trifluoromethylbiphenyl-3-yl group, 2'-trifluoromethylbiphenyl-3-yl group, 4'-trifluoromethylbiphenyl-3-yl group, 5-trifluoromethylbiphenyl-2-yl group, 6-trifluoromethylbiphenyl-2-yl group, 2'-trifluoromethylbiphenyl-2-yl group, 4'-trifluoromethylbiphenyl-2-yl group, 3-ethylbiphenyl-4-yl group, 4'-ethylbiphenyl-4-yl group, 2',4',6'-triethylbiphenyl-4-yl group, 6-ethylbiphenyl-3-yl group, 4'-ethylbiphenyl-3-yl group, 5-ethylbiphenyl-2-yl group, 4'-ethylbiphenyl-2-yl group, 2',4',6'-triethylbiphenyl-2-yl group, 3-propylbiphenyl-4-yl group, 4'-propylbiphenyl-4-yl group, 2',4',6'-tripropylbiphenyl-4-yl group, 6-propylbiphenyl-3-yl group, 4'-propylbiphenyl-3-yl group, 5-propylbiphenyl-2-yl group, 4'-propylbiphenyl-2-yl group, 2',4',6'-tripropylbiphenyl-2-yl group, 3-isopropylbiphenyl-4-yl group, 4'-isopropylbiphenyl-4-yl group, 2',4',6'-triisopropylbiphenyl-4-yl group, 6-isopropylbiphenyl-3-yl group, 4'-isopropylbiphenyl-3-yl group, 5-isopropylbiphenyl-2-yl group, 4'-isopropylbiphenyl-2-yl group, 2',4',6'-triisopropylbiphenyl-2-yl group, 3-butylbiphenyl-4-yl group, 4'-butylbiphenyl-4-yl group, 2',4',6'-tributylbiphenyl-yl group, 6-butylbiphenyl-3-yl group, 4'-butylbiphenyl-3-yl group, 5-butylbiphenyl-2-yl group, 4'-butylbiphenyl-2-yl group, 2',4',6'-tributylbiphenyl-2-yl group, 3-tert-butylbiphenyl-4-yl group, 4'-tert-butylbiphenyl-4-yl group, 2',4',6'-tri-tert-butylbiphenyl-4-yl group, 6-tert-butylbiphenyl-3-yl group, 4'-tert-butylbiphenyl-3-yl group, 5-tert-butylbiphenyl-2-yl group, 4'-tert-butylbiphenyl-2-yl group and 2',4',6'-tri-tert-butylbiphenyl-2-yl group.

Of these, phenyl group is preferable in view of ease in synthesis and the performance as a material for an organic electroluminescent device.

The substituted or unsubstituted aromatic hydrocarbon group, represented by Ar in the general formula (1), includes, for example, substituted or unsubstituted phenyl group, substituted or unsubstituted naphthyl group, substituted or unsubstituted anthryl group, substituted or unsubstituted perylenyl group and substituted or unsubstituted triphenylenyl group. Of these, substituted or unsubstituted phenyl group, and substituted or unsubstituted naphthyl group are preferable in view of the performance as a material for an organic electroluminescent device. Unsubstituted or methyl-substituted or phenyl-substituted or di-phenyl-substituted phenyl group, and a naphthyl group are especially preferable in view of ease in synthesis.

As specific examples of the substituted or unsubstituted aromatic hydrocarbon group, there can be mentioned those which are recited below. The substituted or unsubstituted aromatic hydrocarbon group is not limited thereto.

As specific examples of the substituted or unsubstituted phenyl groups, there can be mentioned a phenyl group (i.e., an unsubstituted phenyl group); and substituted phenyl groups such as p-tolyl group, m-tolyl group, o-tolyl group, 4-trifluoromethylphenyl group, 3-trifluoromethylphenyl group, 2-trifluoromethylphenyl group, 2,4-dimethylphenyl group, 3,5-dimethylphenyl group, 2,6-dimethylphenyl group, mesityl group, 2-ethylphenyl group, 3-ethylphenyl group, 4-ethylphenyl group, 2,4-diethylphenyl group, 3,5-diethylphenyl group, 2-propylphenyl group, 3-propylphenyl group, 4-propylphenyl group, 2,4-dipropylphenyl group, 3,5-dipropylphenyl group, 2-isopropylphenyl group, 3-isopropylphenyl group, 4-isopropylphenyl group, 2,4-diisopropylphenyl group, 3,5-diisopropylphenyl group, 2-butylphenyl group, 3-butylphenyl group, 4-butylphenyl group, 2,4-dibutylphenyl group, 3,5-dibutylphenyl group, 2-tert-butylphenyl group, 3-tert-butylphenyl group, 4-tert-butylphenyl group, 2,4-di-tert-butylphenyl group, 3,5-di-tert-butylphenyl group, 3-chlorophenyl group, 4-chlorophenyl group, 3,4-dichlorophenyl group, 3,5-dichlorophenyl group, 3-bromophenyl group, 4-bromophenyl group, 3,4-dibromophenyl group and 3,5-dibromophenyl group;

unsubstituted biphenylyl groups such as 4-biphenylyl group, 3-biphenylyl group and 2-biphenylyl group; and substituted biphenylyl groups such as 2-methylbiphenyl-4-yl group, 3-methylbiphenyl-4-yl group, 2'-methylbiphenyl-4-yl group, 4'-methylbiphenyl-4-yl group, 2,2'-dimethylbiphenyl-4-yl group, 2',4',6'-trimethylbiphenyl-4-yl group, 6-methylbiphenyl-3-yl group, 5-methylbiphenyl-3-yl group, 2'-methylbiphenyl-3-yl group, 4'-methylbiphenyl-3-yl group, 6,2'-dimethylbiphenyl-3-yl group, 2',4',6'-trimethylbiphenyl-3-yl group, 5-methylbiphenyl-2-yl group, 6-methylbiphenyl-2-yl group, 2'-methylbiphenyl-2-yl group, 4'-methylbiphenyl-2-yl group, 6,2'-dimethylbiphenyl-2-yl group, 2',4',6'-trimethylbiphenyl-2-yl group, 2-trifluoromethylbiphenyl-4-yl group, 3-trifluoromethylbiphenyl-4-yl group, 2'-trifluoromethylbiphenyl-4-yl group, 4'-trifluoromethylbiphenyl-4-yl group, 6-trifluoromethylbiphenyl-3-yl group, 5-trifluoromethylbiphenyl-3-yl group, 2'-trifluoromethylbiphenyl-3-yl group, 4'-trifluoromethylbiphenyl-3-yl group, 5-trifluoromethylbiphenyl-2-yl group, 6-trifluoromethylbiphenyl-2-yl group, 2'-trifluoromethylbiphenyl-2-yl group, 4'-trifluoromethylbiphenyl-2-yl group, 3-ethylbiphenyl-4-yl group, 4'-ethylbiphenyl-4-yl group, 2',4',6'-triethylbiphenyl-4-yl group, 6-ethylbiphenyl-3-yl group, 4'-ethylbiphenyl-3-yl group, 5-ethylbiphenyl-2-yl group, 4'-ethylbiphenyl-2-yl group, 2',4',6'-triethylbiphenyl-2-yl group, 3-propylbiphenyl-4-yl group, 4'-propylbiphenyl-4-yl group, 2',4',6'-tripropylbiphenyl-4-yl group, 6-propylbiphenyl-3-yl group, 4'-propylbiphenyl-3-yl group, 5-propylbiphenyl-2-yl group, 4'-propylbiphenyl-2-yl group, 2',4',6'-tripropylbiphenyl-2-yl group, 3-isopropylbiphenyl-4-yl group, 4'-isopropylbiphenyl-4-yl group, 2',4',6'-triisopropylbiphenyl-4-yl group, 6-isopropylbiphenyl-3-yl group, 4'-isopropylbiphenyl-3-yl group, 5-isopropylbiphenyl-2-yl group, 4'-isopropylbiphenyl-2-yl group, 2',4',6'-triisopropylbiphenyl-2-yl group, 3-butylbiphenyl-4-yl group, 4'-butylbiphenyl-4-yl group, 2',4',6'-tributylbiphenyl-4-yl group, 6-butylbiphenyl-3-yl group, 4'-butylbiphenyl-3-yl group, 5-butylbiphenyl-2-yl group, 4'-butylbiphenyl-2-yl group, 2',4',6'-tributylbiphenyl-2-yl group, 3-tert-butylbiphenyl-4-yl group, 4'-tert-butylbiphenyl-4-yl group, 2',4',6'-tri-tert-butylbiphenyl-4-yl group, 6-tert-butylbiphenyl-3-yl group, 4'-tert-butylbiphenyl-3-yl group, 5-tert-butylbiphenyl-2-yl group, 4'-tert-butylbiphenyl-2-yl group and 2',4',6'-tri-tert-butylbiphenyl-2-yl group;

terphenylyl groups such as 1,1':4',1''-terphenyl-3-yl group, 1,1':4',1''-terphenyl-4-yl group, 1,1':3',1''-terphenyl-3-yl group, 1,1':3',1''-terphenyl-4-yl group, 1,1':3',1''-terphenyl-5'-yl group, 1,1':2',1''-terphenyl-3-yl group, 1,1':2',1''-terphenyl-4-yl group and 1,1':2',1''-terphenyl-4'-yl group; and 3-(1-naphthyl)phenyl group, 4-(1-naphthyl)phenyl group, 3-(2-naphthyl)phenyl group, 4-(2-naphthyl)phenyl group, 3-(1-anthryl)phenyl group, 3-(2-anthryl)phenyl group, 3-(9-anthryl)phenyl group, 4-(1-anthryl)phenyl group, 4-(2-anthryl)phenyl group, 4-(9-anthryl)phenyl group, 3-(1-perylenyl)phenyl group, 3-(2-perylenyl)phenyl group, 4-(1-perylenyl)phenyl group, 4-(2-perylenyl)phenyl group, 3-triphenylenylphenyl group and 4-triphenylenylphenyl group.

Of these, phenyl group, p-tolyl group, m-tolyl group, o-tolyl group, 2,6-dimethylphenyl group, 4-tert-butylphenyl group, 4-biphenylyl group, 3-biphenylyl group, 2-biphenylyl group, 1,1':4',1''-terphenyl-4-yl group, 1,1':2',1''-terphenyl-4-yl group, 1,1':3',1''-terphenyl-5'-yl group, 4-(1-naphthyl)phenyl group and 4-(9-anthryl)phenyl group are preferable in view of the performance as a material for an organic electroluminescent device. p-Tolyl group, 4-biphenylyl group, 2-biphenylyl group and 1,1':3',1"-terphenyl-5'-yl group are especially preferable inview of ease in synthesis.

As specific examples of the substituted or unsubstituted naphthyl groups, there can be mentioned unsubstituted naphthyl groups such as 1-naphthyl group and 2-naphthyl group; and substituted naphthyl groups such as 4-methylnaphthalen-1-yl group, 4-trifluoromethylnaphthalen-1-yl group, 4-ethylnaphthalen-1-yl group, 4-propylnaphthalen-1-yl group, 4-butylnaphthalen-1-yl group, 4-tert-butylnaphthalen-1-yl group, 5-methylnaphthalen-1-yl group, 5-trifluoromethylnaphthalen-1-yl group, 5-ethylnaphthalen-1-yl group, 5-propylnaphthalen-1-yl group, 5-butylnaphthalen-1-yl group, 5-tert-butylnaphthalen-1-yl group, 6-methylnaphthalen-2-yl group, 6-trifluoromethylnaphthalen-2-yl group, 6-ethylnaphthalen-2-yl group, 6-propylnaphthalen-2-yl group, 6-butylnaphthalen-2-yl group, 6-tert-butylnaphthalen-2-yl group, 7-methylnaphthalen-2-yl group, 7-trifluoromethylnaphthalen-2-yl group, 7-ethylnaphthalen-2-yl group, 7-propylnaphthalen-2-yl group, 7-butylnaphthalen-2-yl group and 7-tert-butylnaphthalen-2-yl group.

Of these, 1-naphthyl group, 4-methylnaphthalene-1-yl group, 4-tert-butylnaphthalen-1-yl group, 5-methylnaphthalen-1-yl group, 5-tert-butylnaphthalen-1-yl group, 2-naphthyl group, 6-methylnaphthalen-2-yl group, 6-tert-butylnaphthalen-2-yl group, 7-methylaphthalen-2-yl group and 7-tert-butylnaphthalen-2-yl group are preferable in view of the performance as a material for an organic electroluminescent device. 2-Naphthyl group is especially preferable because of ease in synthesis.

As specific examples of substituted or unsubstituted anthryl groups, substituted or unsubstituted perylenyl groups, and substituted or unsubstituted triphenylenyl groups, which are represented by Ar in the general formula (1), there can be mentioned 1-anthryl group, 2-anthryl group, 9-anthryl group, 1-perylenyl group, 2-perylenyl group and 1-triphenylenyl group.

In the general formula (1), Ar is different from each of the two substituted quarterarylenyl groups bonded to the 1,3,5-triazine ring in the 1,3,5-triazine derivative. If Ar is the same as the two substituted quarterarylenyl groups bonded to the 1,3,5-triazine ring, the 1,3,5-triazine derivative has undesirably enhanced crystalline property, and an organic electroluminescent device having a layer of a thin film composed thereof exhibits poor long life stability at operation.

The process for producing the 1,3,5-triazine derivative of the general formula (1) (which derivative is hereinafter referred to as "compound (1)" when appropriate) will now be described.

The compound (1) can be produced by a process represented by the following reaction scheme including a step 1.

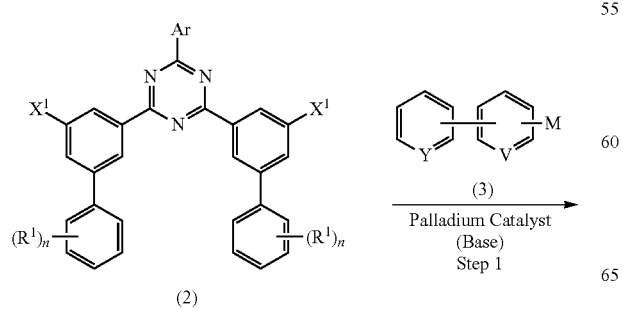

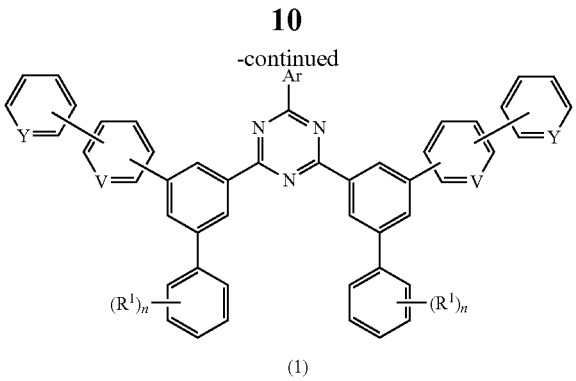

In the general formulae (1), (2) and (3) shown in the above reaction scheme, $R^1$, n, Ar, $X^1$, V, Y and M are the same as defined above.

The leaving group represented by $X^1$ includes, for example, a chlorine atom, a bromine atom and an iodine atom. Of these, a bromine atom and a chlorine atom are preferable because of a high reaction yield.

The above mentioned compound represented by the general formula (2) (which compound is hereinafter referred to as "compound (2)" when appropriate) can be produced by processes specifically described in Reference Example 1 to Reference Example 7, shown below.

The above mentioned compound represented by the general formula (3) (which compound is hereinafter referred to as "compound (3)" when appropriate) can be produced by the processes described in, for example, J. Tsuji: Palladium Reagents and Catalysts, John Wiley & Sons, 2004; Journal of Organic Chemistry, vol. 60, 7508-7510, 1995; Journal of Organic Chemistry, vol. 65, 164-168, 2000; Organic Letters, vol. 10, 941-944, 2008; and Chemistry of Materials, vol. 20, 5951-5953, 2008.

As specific examples of the compound (3), the following 3-1 to 3-37 can be mentioned, but the compound (3) used in the present invention is not limited thereto. In the following compounds, M is a metal-containing group or a hetero atom-containing group.

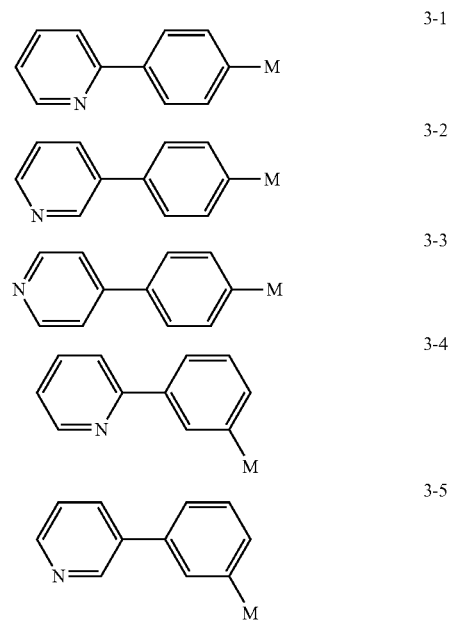

-continued
3-6
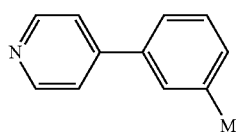
3-7
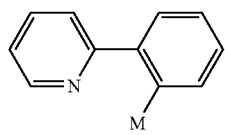
3-8
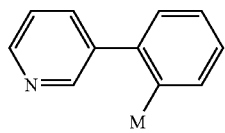
3-9
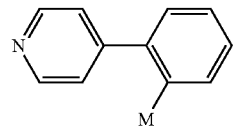
3-10
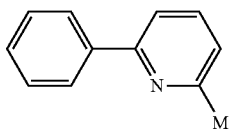
3-11
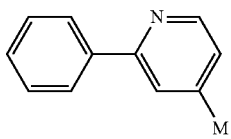
3-12
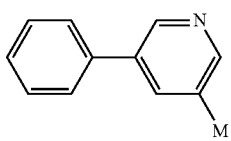
3-13
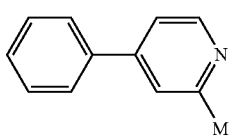
3-14
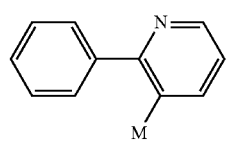
3-15
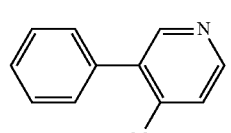
3-16
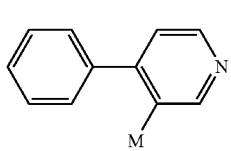
-continued
3-17
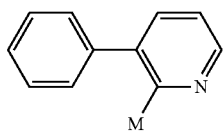
3-18
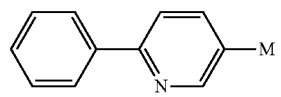
3-19
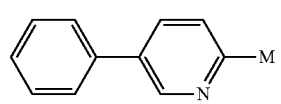
3-20
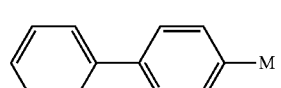
3-21
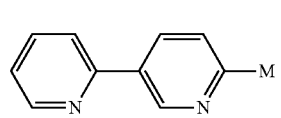
3-22
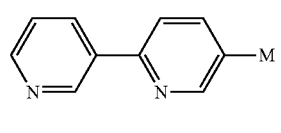
3-23
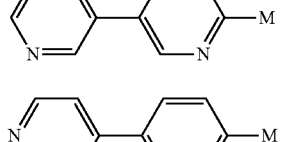
3-24
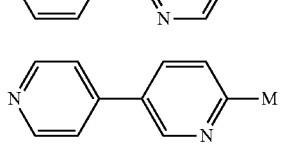
3-25
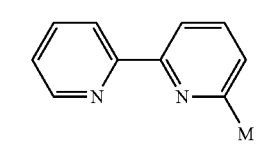
3-26
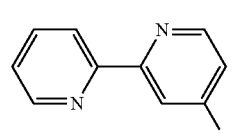
3-27
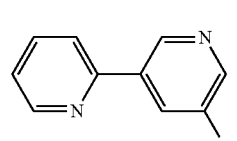
3-28
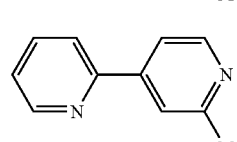
3-29

-continued

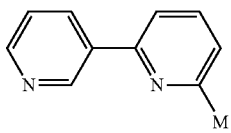
3-30

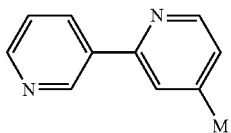
3-31

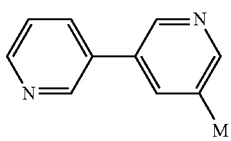
3-32

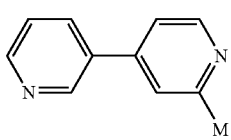
3-33

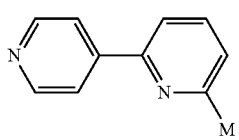
3-34

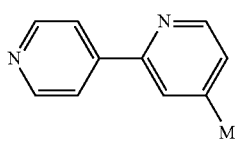
3-35

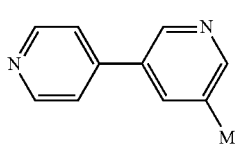
3-36

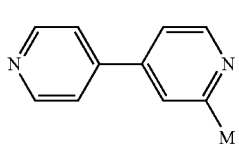
3-37

The metal-containing group represented by M can be selected from those which are conventionally used for general coupling reactions, and said group is not particularly limited. The metal-containing group includes alkali metal atoms, alkaline earth metal atoms and metal atoms in group 8 to group 13. These metal atoms may have a substituent selected from a halogen atom, an alkyl group having 1 to 4 carbon atoms, an aromatic hydrocarbon group having 6 to 10 carbon atoms, an alkoxyl group having 1 to 6 carbon atoms and an aryloxy group having 6 to 10 carbon atoms, and a tertiary amine having 3 to 16 carbon atoms and an aromatic imine having 6 to 20 carbon atoms.

As specific examples of the metal-containing group represented by M, there can be mentioned Li, Na, MgCl, MgBr, MgI, CuCl, CuBr, CuI, AlCl$_2$, AlBr$_2$, Al(Me)$_2$, Al(Et)$_2$, Al($^i$Bu)$_2$, Sn(Me)$_3$, Sn(Bu)$_3$ and ZnR$^2$ (where R$^2$ is a halogen atom).

The ZnR$^2$ includes, for example, ZnCl, ZnBr and ZnI. Of these metal-containing groups, ZnCl is preferable because of high reaction yield. TMEDA, i.e, a complex of ZnCl to which tetramethylethylenediamine has been coordinated, is especially preferable.

The heteroatom-containing group represented by M can be selected from those which are conventionally used for general coupling reactions, and said group is not particularly limited. The hetero atom-containing group includes a boron atom, a silicon atom, a germanium atom and a tin atom. These hetero atoms may have a substituent selected from a halogen atom, an alkyl group having 1 to 4 carbon atoms, an aromatic hydrocarbon group having 6 to 10 carbon atoms, an alkoxyl group having 1 to 6 carbon atoms and an aryloxy group having 6 to 10 carbon atoms.

As specific examples of the hetero atom-containing group represented by M, there can be mentioned Si(Ph)$_3$, SnF$_3$ and B(OR$^3$)$_2$ (where R$^3$ is a hydrogen atom, an alkyl group having 1 to 4 carbon atoms or a phenyl group). The B(OR$^3$)$_2$ includes, for example, B(OH)$_2$, B(OMe)$_2$, B(O$^i$Pr)$_2$, B(OBu)$_2$ and B(OPh)$_2$.

In the formula B(OR)$_2$ represented by M, the two R$^3$s may be the same or different and may form a ring together with the boron atom and the oxygen atoms, bonded to the two R$^3$s. As examples of such B(OR$^3$)$_2$, the following groups (I) through (VI) are mentioned. Of these, the group represented by (II) is preferable in view of high reaction yield.

(I)

(II)

(III)

(IV)

(V)

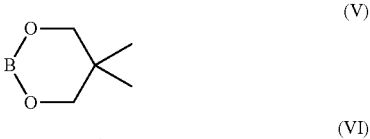
(VI)

In the step 1 in the above-described reaction scheme, compound (2) is reacted with compound (3) in the presence of a palladium catalyst and in the presence or absence of a base to give the 1,3,5-triazine derivative of the present invention. This coupling reaction can be carried out with a good yield under reaction conditions adopted in the conventional coupling reactions such as, for example, Suzuki-Miyaura reaction, Negishi reaction, Tamao-Kumada reaction and Stille reaction.

The palladium catalyst used in the step 1 includes, for example, palladium salts such as palladium chloride, palladium acetate, palladium trifluoroacetate and palladium nitrate; and complex compounds such as t-allylpalladium chloride dimmer, palladium acetylacetonate, tris(dibenzylideneacetone)-dipalladium, dichlorobis(triphenylphosphine)palladium, tetrakis(triphenylphosphine)palladium and dichloro[1,1'-bis(diphenylphosphino)ferrocene]palladium.

Palladium complex compounds having a tertiary phosphine as a ligand are preferably used because they give a high reaction yield. Palladium complex compounds having triphenylphosphine as a ligand are especially preferably used because they are easily available and give a high reaction yield.

The amount of the palladium catalyst used in the step 1 is not particularly limited, provided that it is a so-called catalyst quantity. Preferably the ratio of the amount of the palladium catalyst to the compound (2) is chosen in the range of from 1:50 to 1:10 by mole in view of high reaction yield.

The palladium complex compound having a tertiary phosphine as a ligand can also be prepared by incorporating a tertiary phosphine to a palladium salt or a palladium complex compound in the reaction system.

As specific examples of the tertiary phosphine to be incorporated to a palladium salt or a palladium complex compound, there can be mentioned triphenylphosphine, trimethylphosphine, tributylphosphine, tri(tert-butyl)phosphine, tricyclohexylphosphine, tert-butyldiphenylphosphine, 9,9-dimethyl-4,5-bis(diphenylphosphino)xanthene, 2-(diphenylphosphino)-2'-(N,N-dimethylamino)biphenyl, 2-(di-tert-butylphosphino)biphenyl, 2-(dicyclohexylphosphino)-biphenyl, bis(diphenylphosphino)methane, 1,2-bis(diphenylphosphino)ethane, 1,3-bis(diphenylphosphino)-propane, 1,4-bis(diphenylphosphino)butane, 1,1'-bis(diphenylphosphino)ferrocene, tri-(2-furyl)phosphine, tri-(o-tolyl)phosphine, tris(2,5-xylyl)phosphine, (±)-2,2'-bis(diphenylphosphino)-1,1'-binaphthyl and 2-dicyclohexylphosphino-2',4',6'-triisopropylbiphenyl.

Of these, 2-dicyclohexylphosphino-2',4',6'-triisopropylbiphenhyl and tri(tert-butyl)phosphine are preferable in view of ease in availability and high reaction yield.

The molar ratio of the tertiary phosphine to the palladium salt or the complex compound is preferably in the range of from 1:10 to 10:1, and more preferably from 1:2 to 5:1 because of high reaction yield.

In the reaction in the step 1, when the compound (3) having $B(OR^3)_2$ as a hetero atom-containing compound M is used, i.e., in the case of Suzuki-Miyaura reaction, the reaction yield can be enhanced by carrying out the reaction in the presence of a base.

The base used in the step 1 includes, for example, sodium hydroxide, potassium hydroxide, sodium carbonate, potassium carbonate, lithium carbonate, cesium carbonate, potassium acetate, sodium acetate, potassium phosphate, sodium phosphate, sodium fluoride, potassium fluoride and cesium fluoride. Of these, cesium carbonate and sodium hydroxide are preferable because of high reaction yield. The molar ratio of the base to the compound (3) is preferably in the range of from 1:2 to 10:1, and more preferably from 1:1 to 3:1 because of high reaction yield.

The molar ratio of the compound (2) to the compound (3), which are used in the step 1, is not particularly limited, but is preferably in the range of from 1:1 to 5:1, and more preferably 2:1 to 3:1 because of high reaction yield.

The step 1 can be effected in a reaction medium. The reaction medium used in the step 1 includes, for example, water, dimethylsulfoxide, dimethylformamide, tetrahydrofuran, toluene, benzene, diethyl ether and xylene. These reaction mediums may be used either alone or in combination. Of these, tetrahydrofuran is preferable because of high reaction yield.

The compound (1), produced in the step 1, can be treated by the conventional procedure. If desired, the produced compound is purified by, for example, recrystallization, column chromatography or sublimation.

The compound (1) can also be produced by a method represented by the following reaction scheme including a step 2.

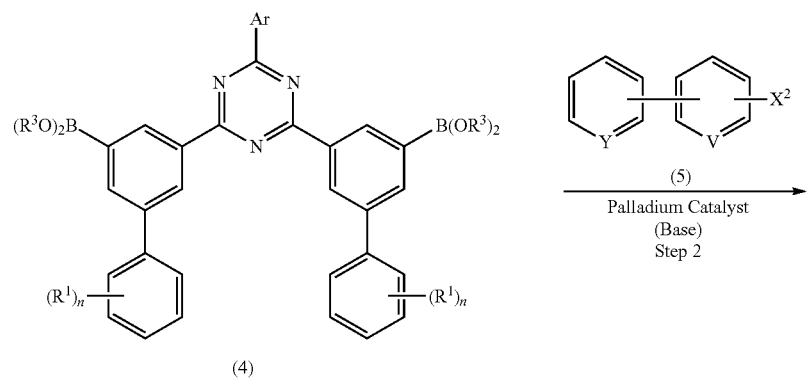

(4)

-continued

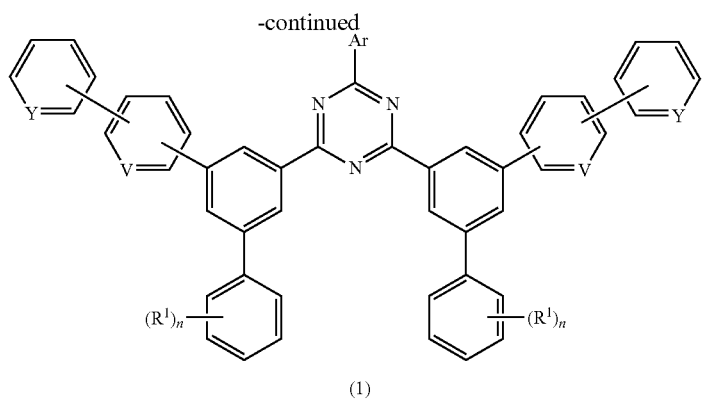

(1)

In the general formulae (1), (4) and (5) shown in the above reaction scheme, $R^1$, $R^3$, n, Ar, V, Y and $X^2$ are the same as defined above.

The leaving group represented by $X^2$ includes, for example, a chlorine atom, a bromine atom and an iodine atom. Of these, a bromine atom is preferable because of a high reaction yield.

The above mentioned compound represented by the general formula (4) (which compound is hereinafter referred to as "compound (4)" when appropriate) can be produced by the method shown in Reference Example 8, shown below.

The above mentioned compound represented by the general formula (5) (which compound is hereinafter referred to as "compound (5)" when appropriate) can be produced by the method described in, for example, Synlett, vol. 6, 852-854, 2003.

As specific examples of the compound (5), the following 5-1 to 5-37 can be mentioned, but the compound (5) used in the present invention is not limited thereto. In the following compounds, $X^2$ is a leaving group.

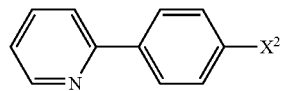
5-1

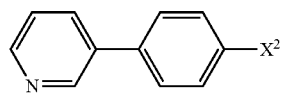
5-2

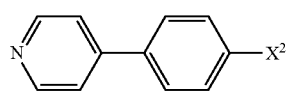
5-3

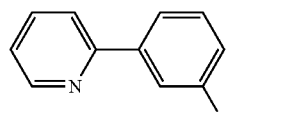
5-4

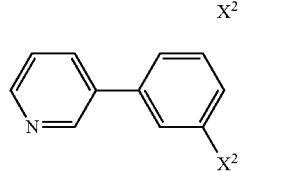
5-5

-continued

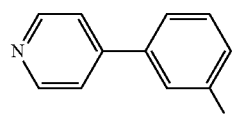
5-6

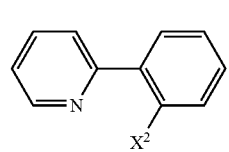
5-7

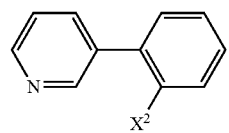
5-8

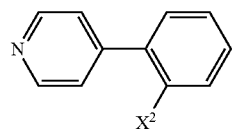
5-9

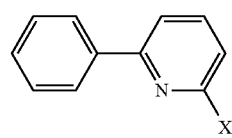
5-10

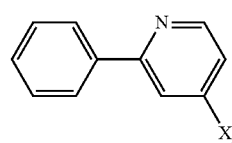
5-11

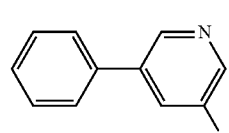
5-12

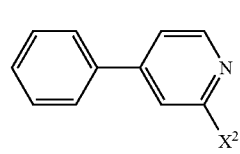
5-13

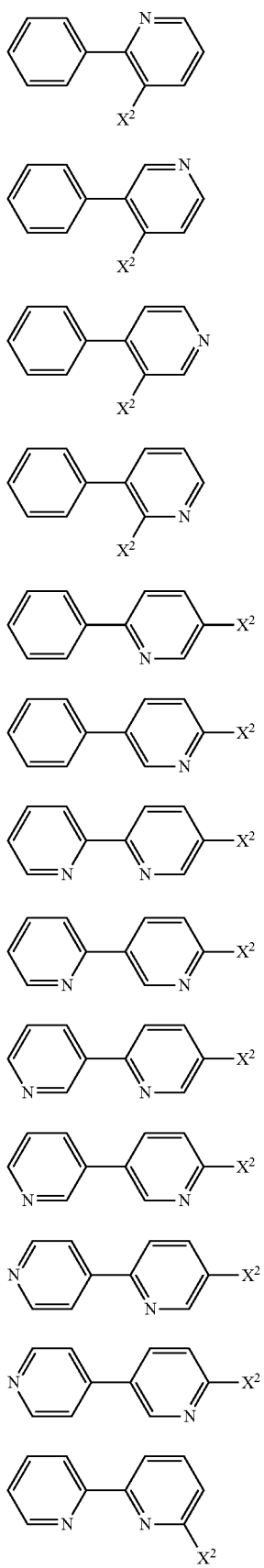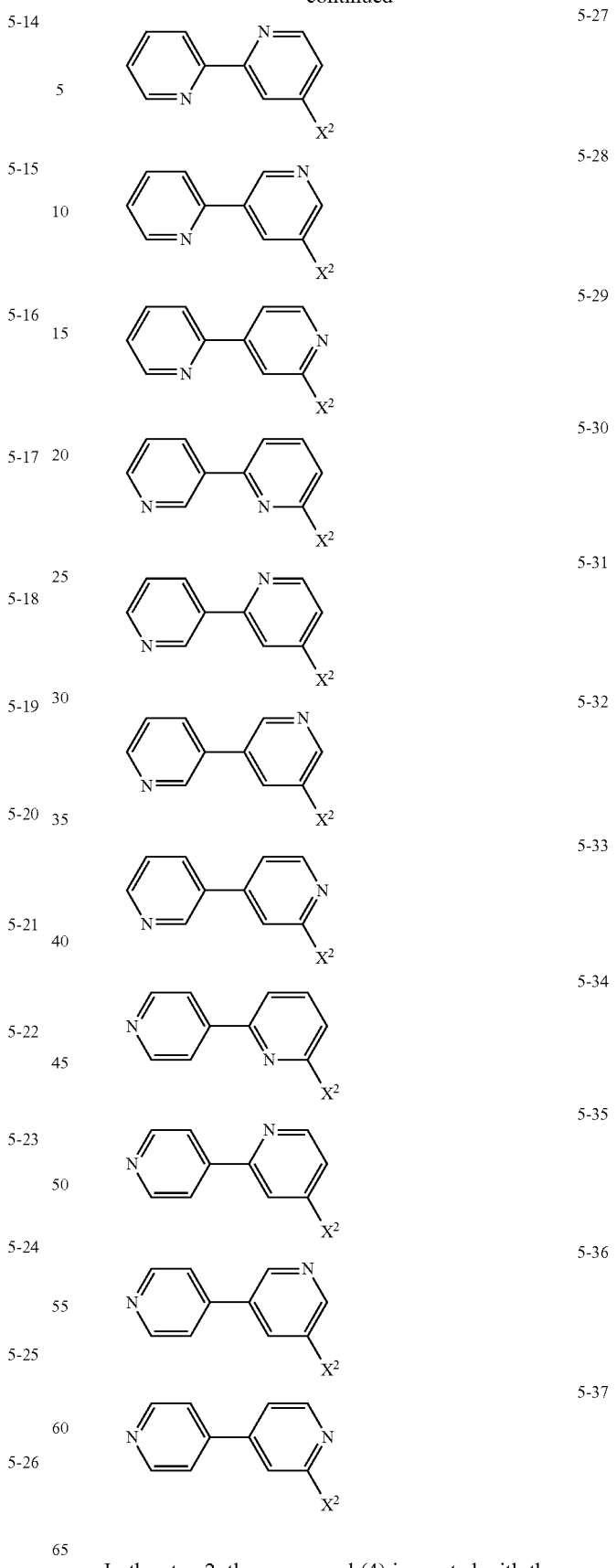
In the step 2, the compound (4) is reacted with the compound (5) in the presence of a palladium catalyst and a base to give the compound (1). The compound (1) can be obtained in a high reaction yield by adopting reaction conditions in the conventional Suzuki-Miyaura reaction.

As examples of the palladium catalyst used in the step 2, those which are recited as examples thereof used in the step 1 are mentioned. Of these, palladium complex compounds having a tertiary phosphine as a ligand are preferable because of high reaction yield. Palladium complex compounds having triphenylphosphine as a ligand are especially preferable because of ease in availability and high reaction yield.

The amount of the palladium catalyst used in the step 2 is not particularly limited, provided that it is a so-called catalyst quantity. In view of the reaction yield, the ratio of the palladium catalyst to the compound (4) is preferably in the range of from 1:50 to 1:10 by mole.

The palladium complex compound having a tertiary phosphine as a ligand can also be prepared by incorporating a tertiary phosphine to a palladium salt or a palladium complex compound in the reaction system.

As specific examples of the tertiary phosphine to be incorporated to a palladium salt or a palladium complex compound, those which are recited with regard to the step 1 can be mentioned. Of these, triphenylphosphine is preferable in view of ease in availability and high reaction yield.

The molar ratio of the tertiary phosphine to the palladium salt or the complex compound is preferably in the range of from 1:10 to 10:1, and more preferably from 1:2 to 5:1 because of high reaction yield.

It is essential to conduct the reaction in the presence of a base in the step 2. As examples of the base used in the step 2, there can be mentioned sodium hydroxide, potassium hydroxide, sodium carbonate, potassium carbonate, lithium carbonate, cesium carbonate, potassium acetate, sodium acetate, potassium phosphate, sodium phosphate, sodium fluoride, potassium fluoride and cesium fluoride. Of these, sodium carbonate is preferable because of high reaction yield. The molar ratio of the base to the compound (4) is not particularly limited, but is preferably in the range of from 1:2 to 10:1, and more preferably from 1:1 to 3:1 because of high reaction yield.

The reaction in the step 2 can be effected in a reaction medium. The reaction medium used includes, for example, water, dimethylsulfoxide, dimethylformamide, tetrahydrofuran, toluene, benzene, diethyl ether, ethanol, methanol and xylene. These reaction mediums may be used either alone or in combination. Of these, a mixed solvent of toluene with water is preferable because of high reaction yield.

The compound (1) produced by the step 2 can be treated by the conventional procedure. If desired, the produced compound is purified by, for example, recrystallization, column chromatography or sublimation.

The compound (4) used as a raw material for the production of the compound (1) in the step 2 can be produced by the following reaction scheme including a step 3.

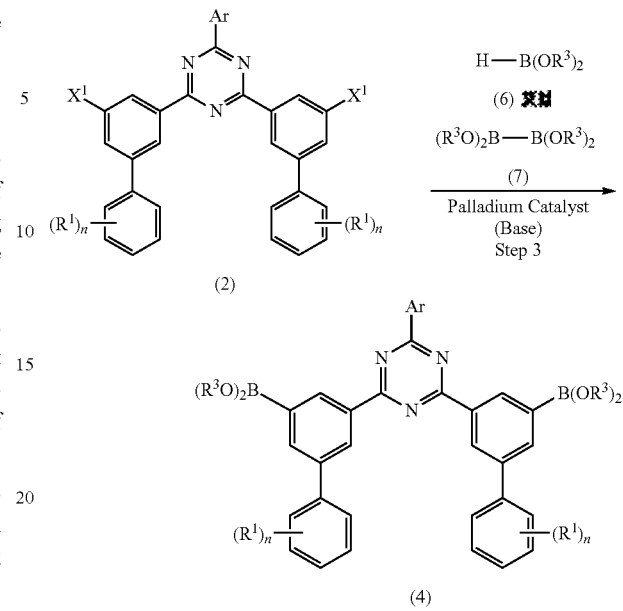

In the general formulae (2) and (4), $R^1$, n, Ar, $X^1$ and $R^3$ are the same as defined above. In the general formulae (6) and (7), $R^3$ is the same as defined above with regard to the general formula (4).

The step 3 is a step of allowing the compound (2) to react with a borane compound represented by the general formula (6) (which compound is hereinafter referred to as "borane compound (6)" when appropriate) or a diboron compound represented by the general formula (7) (which compound is hereinafter referred to as "diboron compound (7)" when appropriate) in the presence of a base and a palladium catalyst to give the compound (4), used in the step 2. This reaction can be effected with a high reaction yield by adopting reaction conditions described in, for example, The Journal of Organic Chemistry, vol. 60, 7508-7510, 1995, or The Journal of Organic Chemistry, vol. 65, 164-168, 2000.

As examples of the palladium catalyst used in the step 3, palladium salts and palladium complex compounds, which are recited as examples thereof used in the step 1 are mentioned. Of these, palladium complex compounds having a tertiary phosphine as a ligand are preferable because of high reaction yield. Palladium complex compounds having triphenylphosphine as a ligand are especially preferable because of ease in availability and high reaction yield.

The amount of the palladium catalyst used in the step 3 is not particularly limited, provided that it is a so-called catalyst quantity. In view of the reaction yield, the ratio of the palladium catalyst to the compound (2) is preferably in the range of from 1:50 to 1:10 by mole.

The palladium complex compound having a tertiary phosphine as a ligand can also be prepared by incorporating a tertiary phosphine to a palladium salt or a palladium complex compound in the reaction system.

As specific examples of the tertiary phosphine to be incorporated to a palladium salt or a palladium complex compound, those which are recited with regard to the step 1 can be mentioned. Of these, triphenylphosphine is preferable in view of ease in availability. The molar ratio of the tertiary phosphine to the palladium salt or the palladium complex compound is preferably in the range of from 1:10 to 10:1, and more preferably from 1:2 to 5:1 because of high reaction yield.

It is essential to conduct the reaction in the presence of a base in the step 3. As examples of the base used in the step 3, there can be mentioned sodium hydroxide, potassium hydroxide, sodium carbonate, potassium carbonate, lithium carbonate, cesium carbonate, potassium acetate, sodium acetate, potassiumphosphate, sodium phosphate, sodium fluoride, potassium fluoride and cesium fluoride. Of these, potassium acetate is preferable because of high reaction yield. The molar ratio of the base to the compound (2) is not particularly limited, but is preferably in the range of from 1:2 to 10:1, and more preferably from 1:1 to 3:1 because of high reaction yield.

The ratio of the borane compound (6) or the diboron compound (7), which are used in the step 3, is not particularly limited, but is preferably in the range of from 1:1 to 5:1 by mole, and more preferably from 2:1 to 3:1 by mole in view of high reaction yield.

The step 3 can be effected in a reaction medium. The reaction medium used includes, for example, water, dimethylsulfoxide, dimethylforamide, tetrahydrofuran, toluene, benzene, diethyl ether, ethanol, methanol and xylene. These reaction mediums may be used either alone or in combination. Of these, tetrahydrofuran is preferable because of high reaction yield.

The compound (4), produced by the step 3, can be isolated after completion of the reaction. Alternatively, the compound (4) can be used without isolation for the step 2.

The process for producing a thin film for an organic electroluminescent device, which film is comprised of the 1,3,5-triazine derivative [compound (1)] according to the present invention, is not particularly limited, but, the thin film can be produced by, for example, vacuum deposition. The vacuum deposition can be conducted using a conventional vacuum deposition apparatus. However, in consideration of the tact time and cost for the production of the organic electroluminescent device, the degree of vacuum at vacuum deposition is preferably in the range of approximately from $1\times10^{-2}$ Pa to $1\times10^{-5}$ Pa which can be achieved by the conventional diffusion pump, turbo-molecular pump or cryopump. The rate of vacuum deposition varies depending upon the thickness of thin film, but the rate is preferably in the range of from 0.005 nm/sec to 1.0 nm/sec.

The solubility of the 1,3,5-triazine derivative (1) in a solvent such as chloroform, dichloromethane, 1,2-dichloroetane, chlorobenzene, toluene, ethyl acetate or tetrahydrofuran is high. Therefore, the thin film can also be made from a solution thereof by, for example, spin coating, ink jetting, casting or dipping using the conventional apparatus.

A thin film comprising the 1,3,5-triazine derivative [compound (1)] according to the present invention has outstanding properties in surface smoothness, amorphousness, heat resistance, electron transportability, hole blocking capability, resistance to oxidation and reduction, moisture resistance, oxygen resistance and electron injection property. Therefore, the thin film is useful as an element constituting an organic electroluminescent device, especially as an element for an electron transport layer, a hole blocking layer and a light emitting host layer of an organic electroluminescent device.

Thus, the thin film comprising the 1,3,5-triazine derivative [compound (1)] according to the present invention is highly expected to be utilized as a constituent of an organic electroluminescent device which is operated at a sufficiently reduced driving voltage and has a long lifetime.

EXAMPLES

The invention will be described more in detail by the following examples and reference examples, that by no means limit the scope of the invention.

Reference Example 1

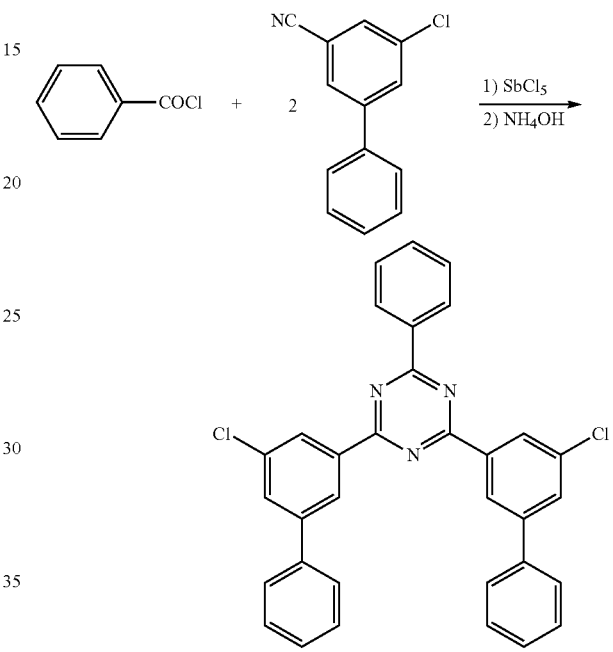

In a stream of argon, a 300 ml three-necked flask equipped with a reflux condenser was charged with benzoyl chloride (4.93 g) and 5-chlorobiphenyl-3-carbonitrile (15.0 g), and then chlorobenzene (100 mL) was added to the content. The thus-obtained solution was cooled to 0° C., and antimony pentachloride (10.5 g) was dropwise added thereto. The resultant mixture was stirred at room temperature for 20 minutes and further at 100° C. for 2 hours. The thus-obtained orange-colored liquid suspension was cooled to −20° C., and an aqueous 28% ammonia solution (50 mL) was added to give a milky white liquid suspension. The suspension was stirred at room temperature overnight, and then, gradually heated to 140° C. in an oil bath to distill away the organic solvent (65 mL) and water (33 mL). Chlorobenzene (100 mL) was added to the solution, and then the solution was filtered at 130° C. The filtrate was left to stand at room temperature, and then methanol (100 mL) was added thereto. The thus-obtained solid precipitate was recovered by filtration, and washed with methanol twice (30 mL×2) and dried. Thus, 12.8 g of 2,4-bis (5-chlorobiphenyl-3-yl)-6-phenyl-1,3,5-triazine was obtained as a white powder (yield 69%).

$^1$H-NMR (CDCl$_3$): δ7.46-7.51 (m, 2H), 7.56 (dd, J=7.8, 7.3 Hz, 4H), 7.59-7.63 (m, 2H), 7.64-7.69 (m, 1H), 7.73 (dd, J=7.8, 1.4 Hz, 4H), 7.81 (dd, J=1.8, 1.6 Hz, 2H), 8.68 (dd, J=1.8, 1.6 Hz, 2H), 8.75 (dd, J=7.0, 1.5 Hz, 2H), 8.84 (dd, J=1.81. 6 Hz, 2H).

$^{13}$C-NMR (CDCl$_3$): δ125.9 (CH×2), 127.3 (CH×4), 127.6 (CH×2), 128.3 (CH×2), 128.8 (CH×2), 129.1 (CH×4), 129.2

(CH×2), 131.3 (CH×2), 133.0 (CH), 135.3 (quart.×2), 135.7 (quart.), 138.1 (quart.×2), 139.4 (quart.×2), 143.4 (quart.×2), 170.7 (quart.×2), 172.0 (quart.).

Reference Example 2

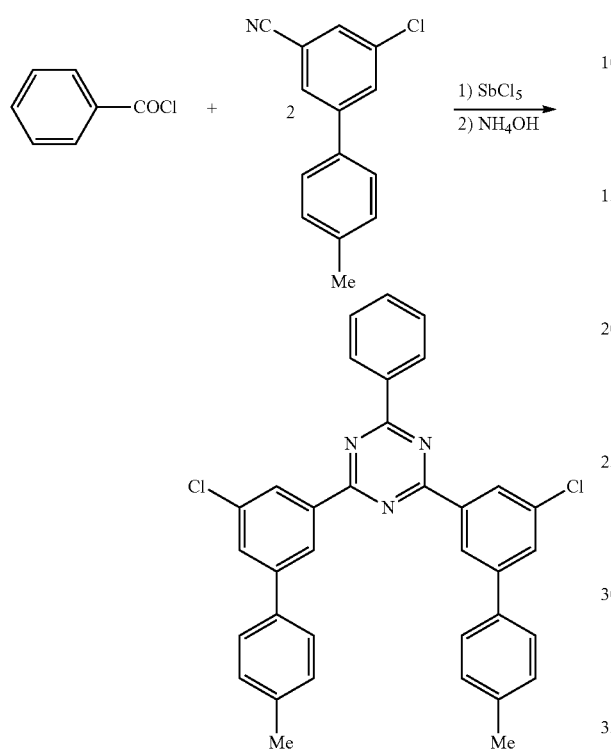

In a stream of argon, a 200 ml three-necked flask equipped with a reflux condenser was charged with benzoyl chloride (1.23 g) and 5-chloro-4'-methylbiphenyl-3-carbonitrile (4.00 g), and then chlorobenzene (40 mL) was added to the content. The thus-obtained solution was cooled to 0° C., and antimony pentachloride (2.63 g) was dropwise added thereto. The resultant mixture was stirred at room temperature for 20 minutes and then refluxed at 100° C. for 2.5 hours. The thus-obtained red-colored solution was cooled to −20° C., and an aqueous 28% ammonia solution (15 mL) was added to obtain a milky white liquid suspension. The suspension was stirred at room temperature overnight, and then, gradually heated to 140° C. in an oil bath to distill away the organic solvent (25 mL) and water (5 mL). Chlorobenzene (50 mL×2) was added to the solution, and then the solution was filtered at 130° C. The filtrate was left to stand at room temperature, and then methanol (100 mL) was added thereto. The thus-obtained solid precipitate was recovered by filtration, and washed with methanol twice (30 mL×2) and dried. Thus, 1.94 g of 2,4-bis(3-chloro-4'-methylbiphenyl-5-yl)-6-phenyl-1,3,5-triazine was obtained as a white powder (yield 390).

$^1$H-NMR (CDCl$_3$): δ2.49 (s, 6H), 7.33-7.39 (m, 1H), 7.37 (d, J=8.0 Hz, 4H), 7.59-7.68 (m, 6H), 7.81 (brs, 2H), 8.68 (dd, J=1.6, 1.8 Hz, 2H), 8.77 (d, J=7.1 Hz, 2H), 8.85 (dd, J=1.5, 1.6 Hz, 2H).

$^{13}$C-NMR (CDCl$_3$): δ21.3 (CH$_3$×2), 125.6 (CH×2), 127.1 (CH×4), 127.3 (CH×2), 128.8 (CH×2), 129.1 (CH×2), 129.8 (CH×4), 131.0 (CH×2), 133.0 (CH), 135.3 (quart.×2), 135.6 (quart.), 136.6 (quart.×2), 138.2 (quart.×2), 138.3 (quart.×2), 143.4 (quart.×2), 170.8 (quart.×2), 172.0 (quart.).

Reference Example 3

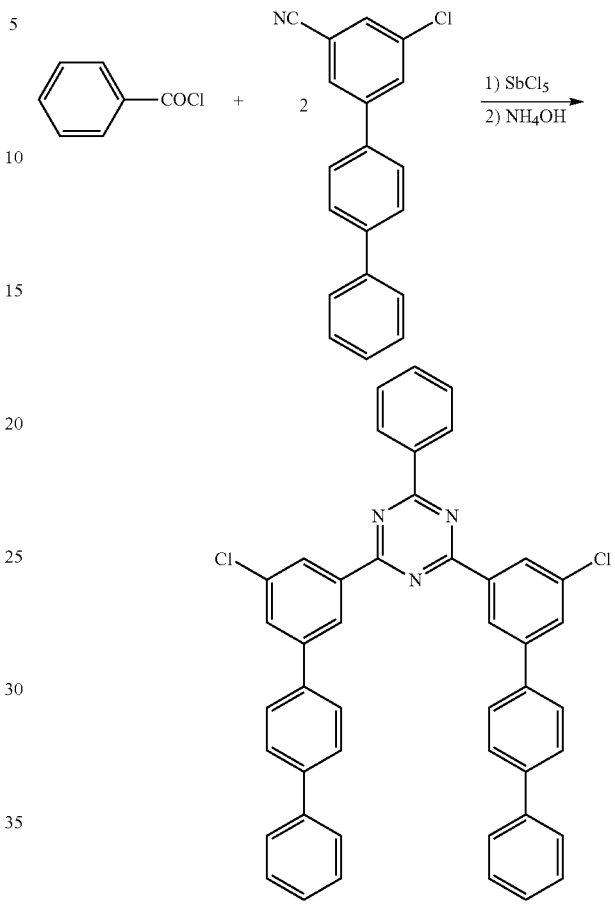

In a stream of argon, a 100 ml three-necked flask equipped with a reflux condenser was charged with benzoyl chloride (218 mg) and 5-chloro-1,1':4':1"-terphenyl-3-carbonitrile (900 mg), and then chlorobenzene (15 mL) was added to the content. The thus-obtained solution was cooled to 0° C., and antimony pentachloride (469 mg) was dropwise added thereto. The resultant mixture was stirred at room temperature for 10 minutes and then refluxed at 100° C. for 3 hours. The thus-obtained black liquid suspension was cooled to −20° C., and an aqueous 28% ammonia solution (4 mL) was added to obtain a brown liquid suspension. The suspension was stirred at room temperature for 12 hours, and then, methanol was added thereto. The thus-obtained solid precipitate was recovered by filtration, and purified by silica gel chromatography using a chloroform/hexane (1:2 to 3:2) mixed liquid as a developing solvent to give 0.052 g of the target 2,4-bis(5-chloro-1,1':4':1"-terhenyl-3-yl)-6-phenyl-1,3,5-triazine as a white powder (yield: 5%).

$^1$H-NMR (CDCl$_3$): δ7.41-7.46 (m, 1H), 7.50-7.55 (m, 1H), 7.62-7.72 (m, 4H), 7.72 (d, J=7.2 Hz, 4H), 7.81 (d, J=8.2 Hz, 4H), 7.85 (d, J=8.2 Hz, 4H), 7.91 (dd, J=1.9, 1.7 Hz, 2H), 8.76 (dd, J=1.9, 1.4 Hz, 2H), 8.84 (brd, J=6.9 Hz, 2H), 8.97 (brs, 2H).

Reference Example 4

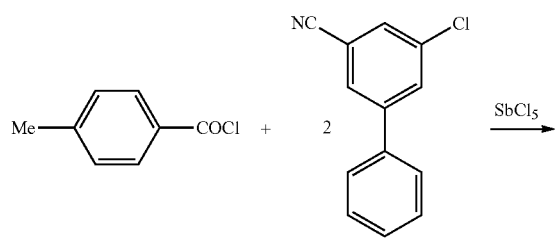

4-Methylbenzoyl chloride (5.42 g) and 5-chlorobiphenyl-3-carbonitrile (15.0 g) were dissolved in chloroform (84 mL). The thus-obtained solution was cooled to 0° C., and antimony pentachloride (10.5 g) was dropwise added thereto. Then the mixture was stirred at room temperature for 10 minutes, and then refluxed for 4 hours. Then the mixture was cooled to room temperature, and the solvent was distilled away under a reduced pressure to give 2,4-bis(5-chlorobiphenyl-3-yl)-6-(4-methylphenyl)-1,3,5-oxadiazin-1-ium=hexachloroantimonic acid as a yellow solid.

The above-mentioned yellow solid was gradually incorporated in an aqueous 28% ammonia solution (300 mL), which was previously cooled to 0° C. and maintained at that temperature, to produce a white solid. The obtained reaction mixture was stirred at room temperature for 1 hour, and then the white solid was recovered by filtration. The recovered white solid was washed with water and with methanol. The washed solid was dried, and chloroform (80 mL) was added. Then the mixture was heated and filtered. The chloroform filtrate was distilled away under reduced pressure, and the obtained solid was recrystallized from dichloromethane-methanol to give 2.81 g of 2,4-bis(5-chlorobiphenyl-3-yl)-6-p-tolyl-1,3,5-triazine as a white solid (yield: 15%).

$^1$H-NMR (CDCl$_3$): δ2.51 (s, 3H), 7.41 (d, J=8.1 Hz, 2H), 7.48 (m, 2H), 7.57 (m, 4H), 7.74 (d, J=7.1 Hz, 4H), 7.83 (dd, J=1.9, 1.5 Hz, 2H), 8.66 (d, J=8.1 Hz, 2H), 8.69 (dd, J=1.9, 1.5 Hz, 2H), 8.86 (t, J=1.5 Hz, 2H).

$^{13}$C-NMR (CDCl$_3$): δ21.8 (CH$_3$), 125.3 (CH×2), 127.3 (CH×4), 127.6 (CH×2), 128.2 (CH×2), 129.0 (CH×4), 129.1 (CH×2), 129.5 (CH×2), 131.1 (CH×2), 133.0 (quart.), 135.3 (quart.×2), 138.3 (quart.×2), 139.5 (quart.×2), 143.5 (quart.×2), 143.7 (quart.), 170.7 (quart.×2), 172.1 (quart.).

Reference Example 5

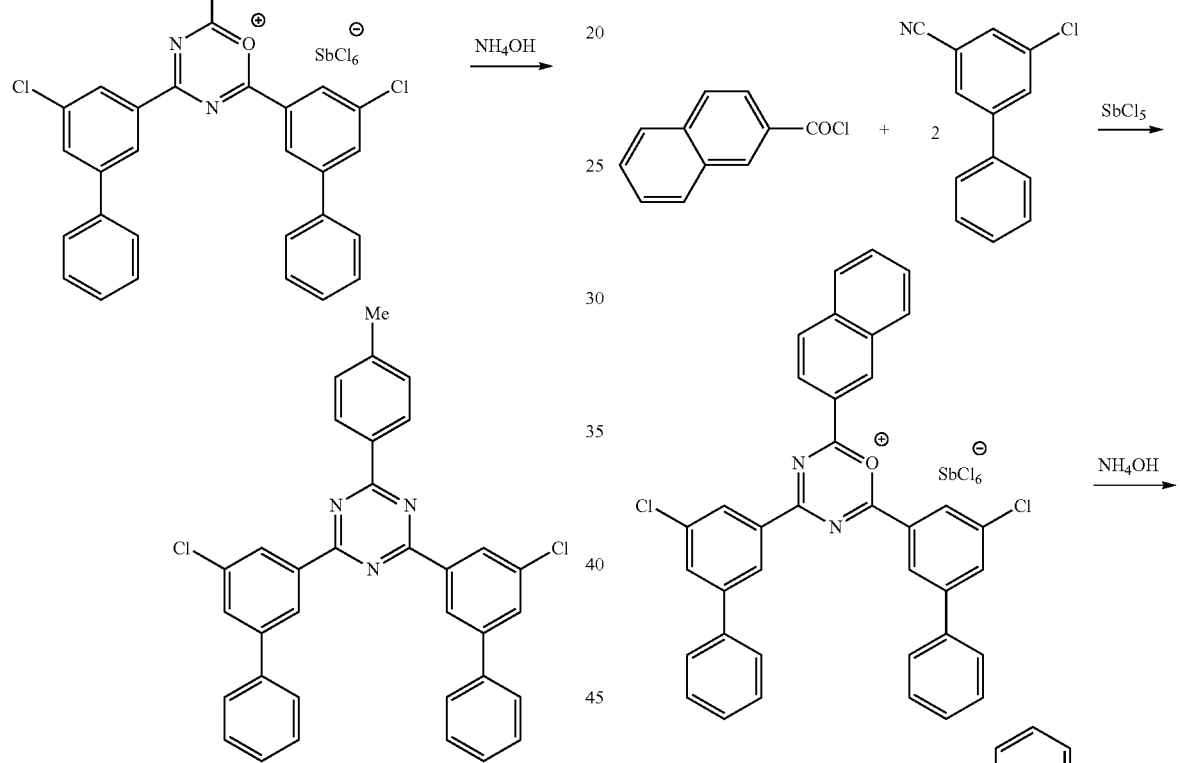

2-Naphthoyl chloride (6.69 g) and 5-chlorobiphenyl-3-carbonitrile (15.0 g) were dissolved in chloroform (84 mL). The thus-obtained solution was cooled to 0° C., and antimony pentachloride (10.5 g) was dropwise added thereto. Then the mixture was stirred at room temperature for 10 minutes, and then refluxed for 7 hours. Then the mixture was cooled to room temperature, and the solvent was distilled away under a reduced pressure to give 2,4-bis(5-chlorobiphenyl-3-yl)-6-(2-naphthyl)-1,3,5-oxadiazin-1-ium=hexachloroantimonic acid as a yellow solid.

The above-mentioned yellow solid was gradually incorporated in an aqueous 28% ammonia solution (300 mL), which was previously cooled to 0° C. and maintained at that temperature, to give a white solid. The obtained reaction mixture was stirred at room temperature for 1 hour, and then the white solid was recovered by filtration. The recovered white solid was washed with water and with methanol. The washed solid was dried, and chloroform (300 mL) was added to the solid. Then the mixture was heated and filtered. Chloroform (100 mL) was added to the filtration residue, and the obtained mixture was heated and filtered. All of the filtrates were collected together, and chloroform was distilled away under reduced pressure from the filtrate mixture. The obtained solid was recrystallized from xylene to give 7.80 g of 2,4-bis(5-chlorobiphenyl-3-yl)-6-(2-naphthyl)-1,3,5-triazine as a white solid (yield: 36%).

$^1$H-NMR (CDCl$_3$): δ7.47-7.53 (m, 2H), 7.55-7.62 (m, 4H), 7.59-7.68 (m, 2H), 7.76 (brd, J=7.2 Hz, 4H), 7.85 (dd, J=1.9, 1.7 Hz, 2H), 7.97 (d, J=7.8 Hz, 1H), 8.05 (d, J=8.6 Hz, 1H), 8.15 (d, J=8.7 Hz, 1H), 8.76 (dd, J=1.7, 1.5 Hz, 2H), 8.81 (dd, J=8.6, 1.5 Hz, 1H), 8.91 (brs, 2H), 9.33 (brs, 1H).

$^{13}$C-NMR (CDCl$_3$): δ125.0 (CH), 125.9 (CH×2), 126.6 (CH), 127.3 (CH×4), 127.6 (CH×2), 127.9 (CH), 128.2 (CH), 128.3 (CH×2), 128.6 (CH), 129.1 (CH×4), 129.7 (CH), 130.3 (CH), 131.3 (CH×2), 132.9 (quart.), 133.1 (quart.), 135.4 (quart.×2), 135.9 (quart.), 138.3 (quart.×2), 139.5 (quart.×2), 144.5 (quart.×2), 170.9 (quart.×2), 172.1 (quart.).

Reference Example 6

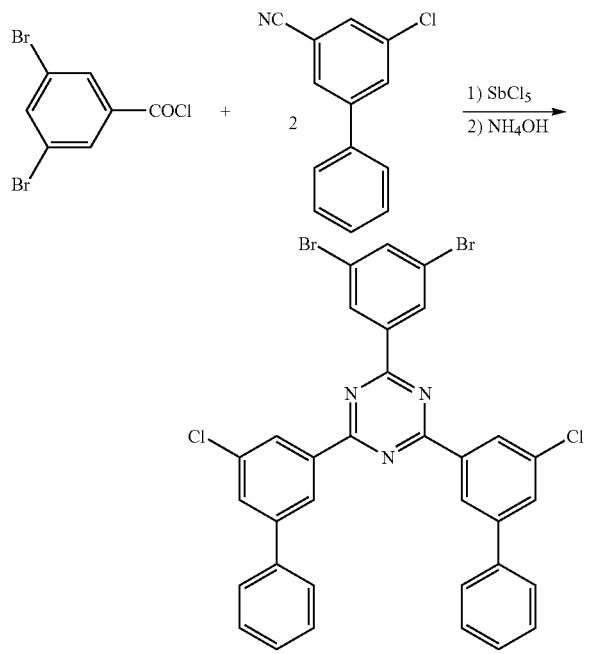

In a stream of argon, a 300 ml three-necked flask equipped with a reflux condenser was charged with 3,5-dibromobenzoyl chloride (10.5 g) and 5-chlorobiphenyl-3-carbonitrile (15.0 g), and then chlorobenzene (100 mL) was added to the content. The thus-obtained solution was cooled to 0° C., and antimony pentachloride (10.5 g) was dropwise added thereto. The resultant mixture was stirred at room temperature for 20 minutes and then refluxed at 100° C. for 2.5 hours. The thus-obtained red-colored solution was cooled to −20° C., and an aqueous 28% ammonia solution (50 mL) was added to obtain a milky white liquid suspension. The suspension was stirred at room temperature for 3 hours, and then, gradually heated to 140° C. in an oil bath to distill away the organic solvent (80 mL) and water (28 mL). Chlorobenzene (100 mL×3) was added to the solution, and then the solution was filtered at 130° C. The filtrate was left to stand at room temperature, and then methanol (300 mL) was added thereto. The thus-obtained solid precipitate was collected by filtration, and washed with methanol twice (50 mL×2) and dried. Thus, 2.21 g of 4,6-bis(5-chlorobiphenyl-3-yl)-2-(3,5-dibromophenyl)-1,3,5-triazine was obtained as a white powder (yield: 9%).

$^1$H-NMR (CDCl$_3$): δ7.37 (brt, J=7.1 Hz, 2H), 7.44 (brt, J=7.1 Hz, 4H), 7.59 (brdd, J=8.1, 1.6 Hz, 4H), 7.69 (t, J=1.7 Hz, 2H), 7.79 (t, J=1.8H z, 1H), 8.47 (t, J=1.7 Hz, 2H), 8.60 (t, J=1.8 Hz, 2H), 8.63 (t, J=1.7 Hz, 2H).

Reference Example 7

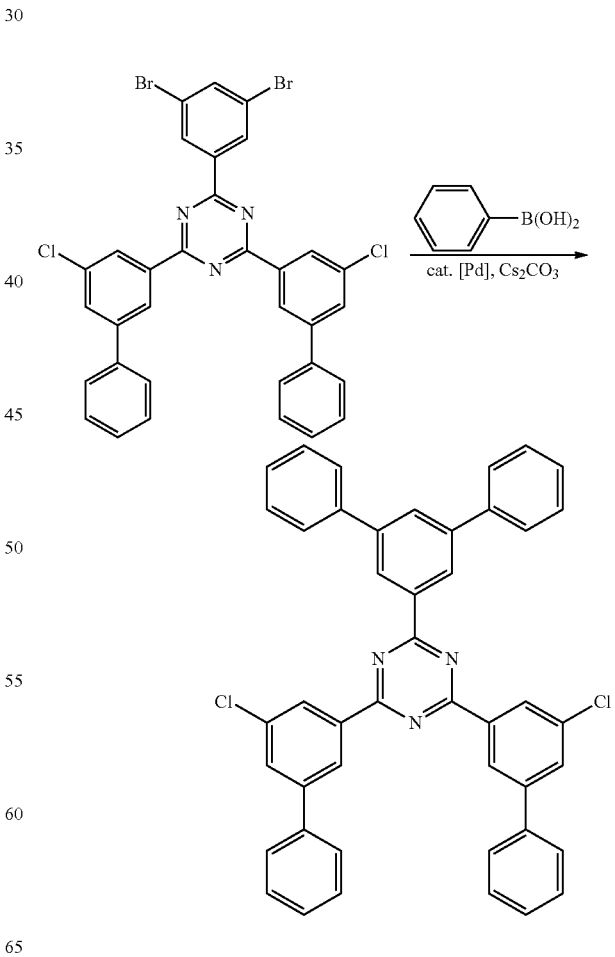

In a stream of argon, phenylboronic acid (904 mg), 4,6-bis(5-chlorobiphenyl-3-yl)-2-(3,5-dibromophenyl)-1,3,5-triazine (1.70 g), cesium carbonate (2.41 g) and tetrakis(triphenylphosphine)palladium (114 mg) were suspended in tetrahydrofuran (80 mL), and the mixture was refluxed for 18 hours. The reaction mixture was left to stand at room temperature, and then low-boiling ingredients were distilled away under a reduced pressure. Methanol was added to the reaction mixture, and the solid precipitate was recovered by filtration, and purified by silica gel chromatography using a chloroform/hexane (1:2 to 1:0) mixed liquid as a developing solvent to give 1.42 g of the target 2,4-bis(5-chlorobiphenyl-3-yl)-6-[(1,1':3',1")-terphenyl-5'-yl]-1,3,5-triazine as a yellowish white powder (yield: 84%).

$^1$H-NMR (CDCl$_3$): δ7.35-7.51 (m, 12H), 7.65 (brd, J=6.8 Hz, 4H), 7.62-7.71 (m, 6H), 7.99 (t, J=1.7 Hz, 1H), 8.62 (t, J=1.5 Hz, 2H), 8.82 (t, J=1.5 Hz, 2H), 8.87 (t, J=1.7 Hz, 2H).

Reference Example 8

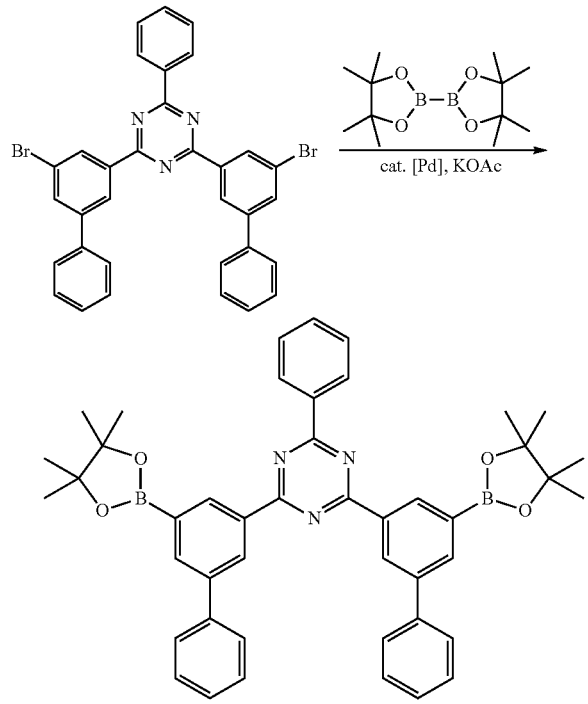

In a stream of argon, 2,4-bis(5-bromobiphenyl-3-yl)-6-phenyl-1,3,5-triazine (3.00 g), bispinacolatediboron (2.70 g), potassium acetate (2.09 g) and dichlorobistriphenylphosphinepalladium (II) (0.136 g) were suspended in tetrahydrofuran (100 mL), and the suspension was refluxed for 21 hours. The reaction mixture was left to stand at room temperature, and then low-boiling ingredients were distilled away under a reduced pressure. Chloroform (100 mL) was added to the obtained solid. An organic phase was washed with water (100 mL) and then dried over magnesium sulfate. Magnesium sulfate was filtered off, and then chloroform was distilled away under a reduced pressure. The obtained crude product was purified by silica gel chromatography using chloroform as a developing solvent to give 2.77 g of the target 2-phenyl-4,6-bis[5-(4,4,5,5-tetramethyl-1,3,2-dioxabororan-2-yl)biphenyl-3-yl]-1,3,5-triazine as a yellow solid (yield: 80%).

$^1$H-NMR (CDCl$_3$): δ1.49 (s, 24H), 7.33 (tt, J=7.3, 1.4 Hz, 2H), 7.44 (t, J=7.3 Hz, 4H), 7.51-7.57 (m, 3H), 7.74 (brdd, J=7.3, 1.4 Hz, 4H), 8.23 (dd, J=1.8, 1.2 Hz, 2H), 8.77 (brdd, J=7.3, 1.4 Hz, 2H), 9.06 (t, J=1.8 Hz, 2H), 9.11 (brdd, J=1.8, 1.2 Hz, 2H).

Example 1

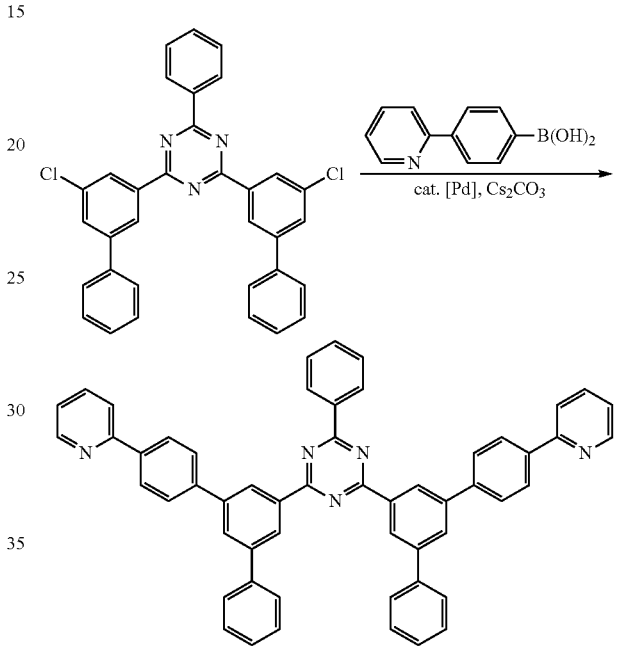

In a stream of argon, 4-(2-pyridyl)phenylboronic acid (2.25 g), 2,4-bis(5-chlrobiphenyl-3-yl)-6-phenyl-1,3,5-triazine (2.00 g), cesium carbonate (3.68 g), palladium acetate (33.9 mg) and 2-dicyclohexylphosphino-2',4',6'-triisopropylbiphenyl (143 mg) were suspended in tetrahydrofuran (150 mL), and the suspension was refluxed for 19 hours. The reaction mixture was left to stand at room temperature, and then low-boiling ingredients were distilled away under a reduced pressure. Methanol was added to the obtained solid. The solid precipitate was recovered by filtration, and the obtained crude product was purified by silica gel chromatography using a methanol/chloroform (1:100-1:75) mixed liquid as a developing solvent to give 2.47 g of the target 6-phenyl-2,4-bis[4-(2-pyridyl)-1,1':3',1"-terphenyl-5'-yl]-1,3,5-triazine as a white powder (yield: 850).

$^1$H-NMR (CDCl$_3$): δ7.26-7.30 (m, 2H), 7.45 (brt, J=7.3 Hz, 2H), 7.53-7.64 (m, 7H), 7.79-7.85 (m, 8H), 7.93 (d, J=8.4 Hz, 4H), 8.12 (t, J=1.7 Hz, 2H), 8.19 (d, J=8.4 Hz, 4H), 8.75 (brd, J=5.0 Hz, 2H), 8.84 (brdd, J=7.5, 1.7 Hz, 2H), 9.01 (t, J=1.7 Hz, 2H), 9.06 (t, J=1.7 Hz, 2H).

$^{13}$C-NMR (CDCl$_3$): δ120.6 (CH×2), 122.3 (CH×2), 126.6 (CH×2), 126.9 (CH×2), 127.6 (CH×4), 127.7 (CH×4), 127.78 (CH×4), 127.81 (CH×2), 128.7 (CH×2), 129.0 (CH×4), 129.1 (CH×2), 130.1 (CH×2), 132.7 (CH), 136.0 (quart.×2), 136.9 (CH×2), 137.4 (quart.×2), 138.8 (quart.×2), 140.8 (quart.×2), 141.2 (quart.), 141.4 (quart.×2), 142.4 (quart.×2), 149.8 (CH×2), 157.0 (quart.×2), 171.76 (quart.×2), 171.84 (quart.).

Example 2

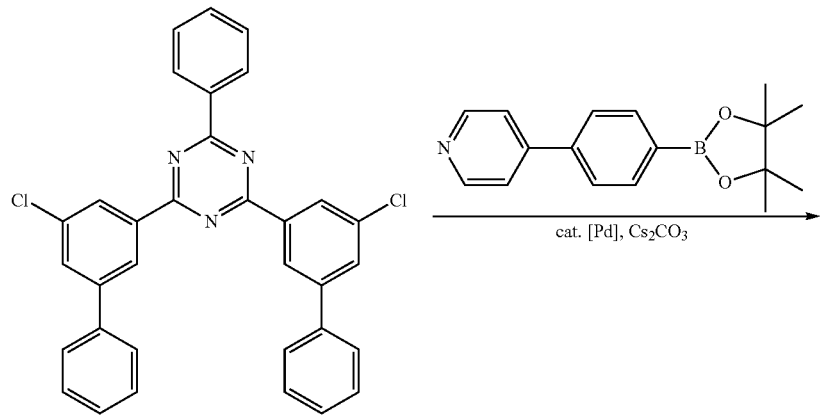

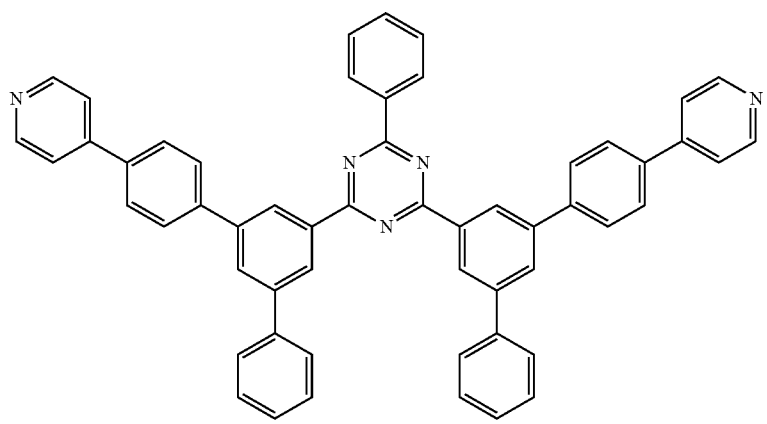

In a stream of argon, 4-[4-(4,4,5,5-tetramethyl-1,3,2-dioxaboroaran-2-yl)phenyl]pyridine (420 mg), 2,4-bis(5-chlrobiphenyl-3-yl)-6-phenyl-1,3,5-triazine (263 mg), cesium carbonate (485 mg), palladium acetate (5.6 mg) and 2-dicyclohexylphosphino-2',4',6'-triisopropylbiphenyl (23.7 mg) were suspended in tetrahydrofuran (15 mL), and the suspension was refluxed for 22 hours. The reaction mixture was left to stand at room temperature, and then low-boiling ingredients were distilled away under a reduced pressure. Methanol was added to the obtained solid. The solid precipitate was recovered by filtration, and the obtained crude product was purified by silica gel chromatography using a methanol/chloroform (1:100-1:50) mixed liquid as a developing solvent to give 232 mg of the target 6-phenyl-2,4-bis[4-(4-pyridyl)-1,1':3',1''-terphenyl-5'-yl]-1,3,5-triazine as a white powder (yield: 61%).

$^1$H-NMR (CDCl$_3$): δ7.49 (brt, J=7.1 Hz, 2H), 7.57 (d, J=7.5 Hz, 4H), 7.61-7.66 (m, 7H), 7.82-7.86 (m, 8H), 7.94 (d, J=8.5 Hz, 4H), 8.10 (t, J=1.7 Hz, 2H), 8.73 (dd, J=4.5, 1.6 Hz, 4H), 8.84 (brdd, J=7.7, 1.7 Hz, 2H), 9.04 (d, J=1.7 Hz, 4H).

$^{13}$C-NMR (CDCl$_3$): δ121.5 (CH×4), 126.5 (CH×2), 127.1 (CH×2), 127.4 (CH×4), 127.6 (CH×4), 127.9 (CH×2), 128.1 (CH×4), 128.7 (CH×2), 129.0 (CH×4), 129.1 (CH×2), 130.0 (CH×2), 132.8 (CH), 136.1 (quart.), 137.5 (quart.×2), 137.6 (quart.×2), 140.7 (quart.×2), 141.4 (quart.×2), 141.6 (quart.×2), 142.6 (quart.×2), 147.8 (quart.×2), 150.4 (CH×4), 171.8 (quart.×2), 171.9 (quart.).

Example 3

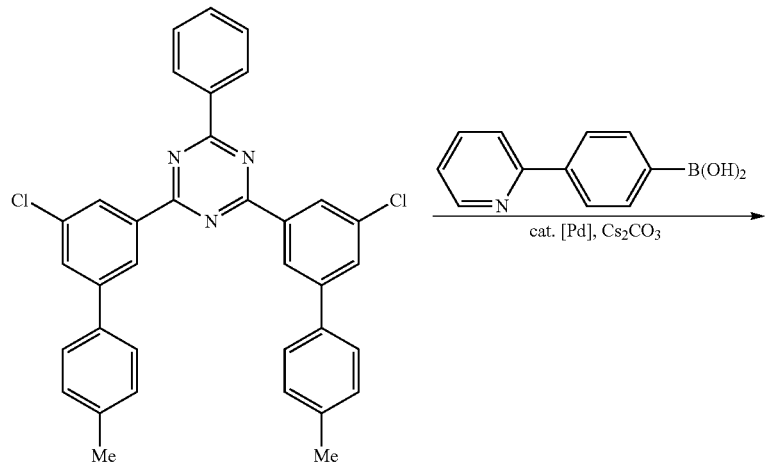

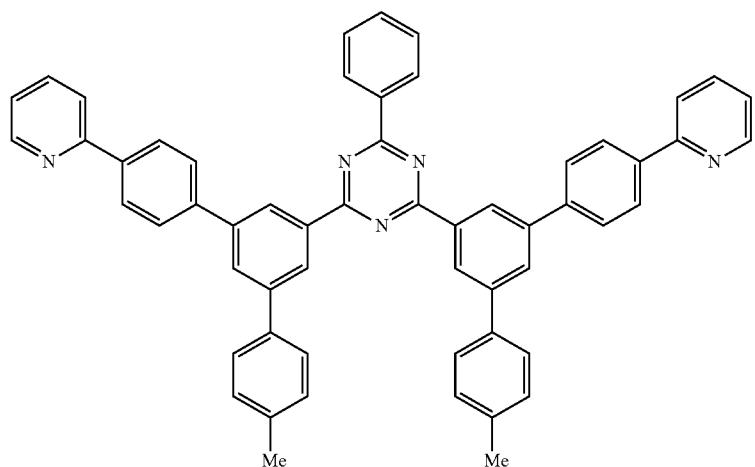

In a stream of argon, 4-(2-pyridyl)phenylboronic acid (2.47 g), 2,4-bis(5-chlro-4'-methylbiphenyl-3-yl)-6-phenyl-1,3,5-triazine (2.30 g), cesium carbonate (4.04 g), palladium acetate (37.0 mg) and 2-dicyclohexylphosphino-2',4',6'-triisopropylbiphenyl (157 mg) were suspended in tetrahydrofuran (200 mL), and the suspension was refluxed for 17 hours. The reaction mixture was left to stand at room temperature, and then low-boiling ingredients were distilled away under a reduced pressure. Methanol was added to the obtained solid. The solid precipitate was recovered by filtration, and the obtained crude product was purified by silica gel chromatography using a methanol/chloroform (0:100-1:100) mixed liquid as a developing solvent to give 3.10 g of the target 6-phenyl-2,4-bis[4-(2-pyridyl)-4''-methyl-1,1':3',1''-terphenyl-5'-yl]-1,3,5-triazine as a white powder (yield: 95%).

$^1$H-NMR (CDCl$_3$): δ2.46 (s, 6H), 7.24-7.30 (m, 2H), 7.36 (d, J=8.0 Hz, 4H), 7.57-7.65 (m, 3H), 7.72 (d, J=8.0 Hz, 4H), 7.78-7.85 (m, 4H), 7.92 (d, J=8.4 Hz, 4H), 8.09 (t, J=1.6 Hz, 2H), 8.18 (d, J=8.4 Hz, 4H), 8.74 (brd, J=4.6 Hz, 2H), 8.83 (brdd, J=7.6, 1.6 Hz, 2H), 8.99 (t, J=1.6 Hz, 2H), 9.02 (t, J=1.6 Hz, 2H).

$^{13}$C-NMR (CDCl$_3$): δ21.3 (CH$_3$×2), 120.6 (CH×2), 122.2 (CH×2), 126.4 (CH×2), 126.8 (CH×2), 127.3 (CH×4), 127.5 (CH×4), 127.8 (CH×4), 128.7 (CH×2), 129.1 (CH×2), 129.7 (CH×4), 130.0 (CH×2), 132.7 (CH), 136.1 (quart.×2), 136.8 (CH×2), 137.4 (quart.×2), 137.6 (quart.×2), 137.9 (quart.×2), 138.7 (quart.), 141.7 (quart.×2), 141.8 (quart.×2), 142.8 (quart.×2), 149.8 (CH×2), 157.0 (quart.×2), 171.82 (quart.×2), 171.84 (quart.).

Example 4

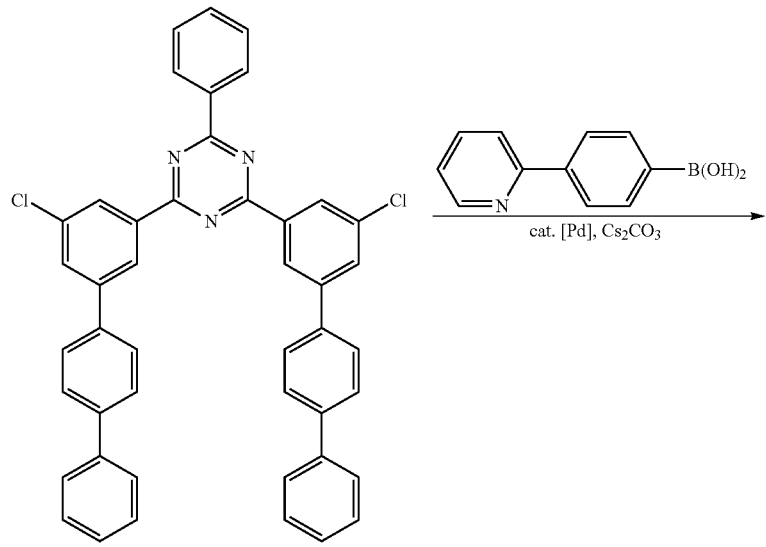

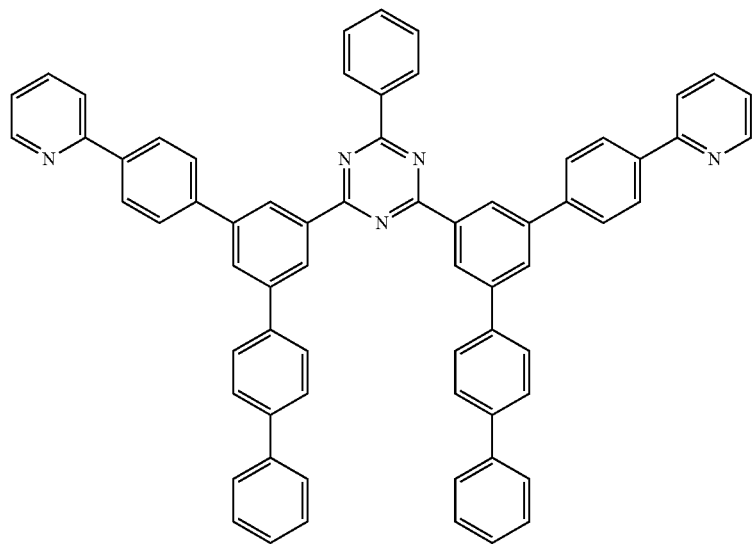

In a stream of argon, 4-(2-pyridyl)phenylboronic acid (116 mg), 2,4-bis(5-chlro-1,1':4':1"-terphenyl-3-yl)-6-phenyl-1,3,5-triazine (100 mg), cesium carbonate (190 mg), palladium acetate (3.3 mg) and 2-dicyclohexylphosphino-2',4',6'-triisopropylbiphenyl (14 mg) were suspended in tetrahydrofuran (15 mL), and the suspension was refluxed for 17 hours. The reaction mixture was left to stand at room temperature, and then low-boiling ingredients were distilled away under a reduced pressure. Methanol was added to the obtained solid. The solid precipitate was recovered by filtration, and the obtained crude product was purified by silica gel chromatography using a methanol/chloroform (0:100-1:100) mixed liquid as a developing solvent to give 125 mg of the target 6-phenyl-2,4-bis[4-(2-pyridyl)-1,1':3',1":4",1'''-quaterphenyl-5'-yl]-1,3,5-triazine as a white powder (yield: 93%).

$^1$H-NMR (CDCl$_3$): δ7.19-7.22 (m, 2H), 7.29-7.35 (m, 2H), 7.42 (brt, J=7.3 Hz, 4H), 7.55-7.65 (m, 7H), 7.71-7.79 (m, 8H), 7.85 (d, J=7.3 Hz, 4H), 7.88 (d, J=8.4 Hz, 4H), 8.10 (t, J=1.8 Hz, 2H), 8.13 (d, J=8.4 Hz, 4H), 8.68 (brd, J=4.7 Hz, 2H), 8.78 (brd, J=7.9 Hz, 2H), 9.01 (d, J=1.7 Hz, 4H).

Example 5

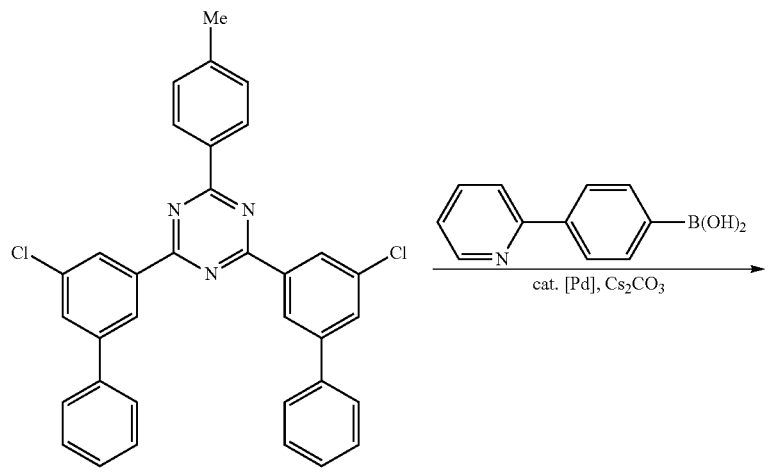

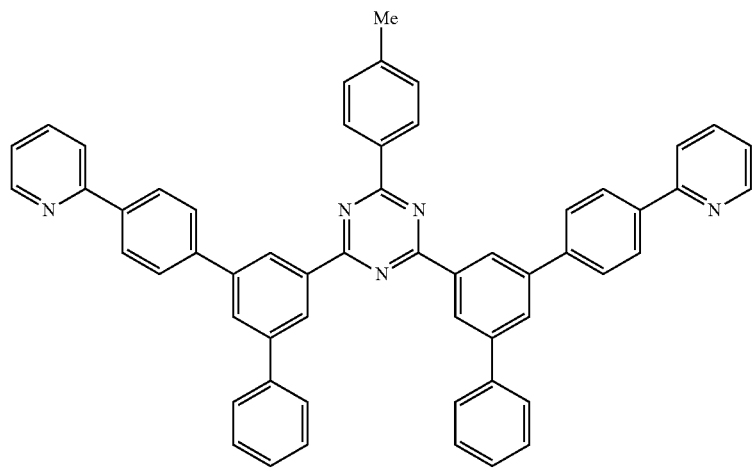

In a stream of argon, 4-(2-pyridyl)phenylboronic acid (1.21 g), 2,4-bis(5-chlorobiphenyl-3-yl)-6-p-tolyl-1,3,5-triazine (1.50 g), cesium carbonate (1.97 g), palladium acetate (24.7 mg) and 2-dicyclohexylphosphino-2',4',6'-triisopropyl-1,1'-biphenyl (105 mg) were suspended in tetrahydrofuran (135 mL), and the suspension was refluxed for 16 hours. The reaction mixture was left to stand at room temperature, and then low-boiling ingredients were distilled away under a reduced pressure. Methanol was added to the obtained solid. The solid precipitate was recovered by filtration, and the obtained crude product was purified by silica gel chromatography using a hexane/chloroform (2:3) mixed liquid as a developing solvent to give 1.85 g of the target 2,4-bis[4-(2-pyridyl)-1,1':3',1''-terphenyl-5'-yl]-6-p-tolyl-1,3,5-triazine as a white powder (yield: 86%).

$^1$H-NMR (CDCl$_3$): δ2.41 (s, 3H), 7.16-7.22 (m, 2H), 7.31 (brd, J=8.1 Hz, 2H), 7.37 (brt, J=7.3 Hz, 2H), 7.47 (brt, J=7.3 Hz, 4H), 7.67-7.76 (m, 8H), 7.83 (d, J=8.4 Hz, 4H), 8.00 (t, J=1.6 Hz, 2H), 8.09 (d, J=8.4 Hz, 4H), 8.62 (d, J=8.2 Hz, 2H), 8.67 (brddd, J=4.6, 1.3, 1.3 Hz, 2H), 8.91 (t, J=1.6 Hz, 2H), 8.94 (t, J=1.6 Hz, 2H). $^{13}$C-NMR (CDCl$_3$): δ21.8 (CH$_3$), 120.5 (CH×2), 122.2 (CH×2), 126.6 (CH×2), 126.9 (CH×2), 127.45 (CH×4), 127.47 (CH×4), 127.7 (CH×4), 127.8 (CH×2), 129.0 (CH×4), 129.1 (CH×2), 129.5 (CH×2), 130.0 (CH×2), 133.5 (quart.), 136.8 (CH×2), 137.6 (quart.×2), 138.8 (quart.×2), 140.9 (quart.×2), 141.4 (quart.×2), 141.7 (quart.×2), 142.4 (quart.×2), 143.4 (quart.), 149.8 (CH×2), 157.1 (quart.×2), 171.7 (quart.×2), 171.9 (quart.).

Example 6

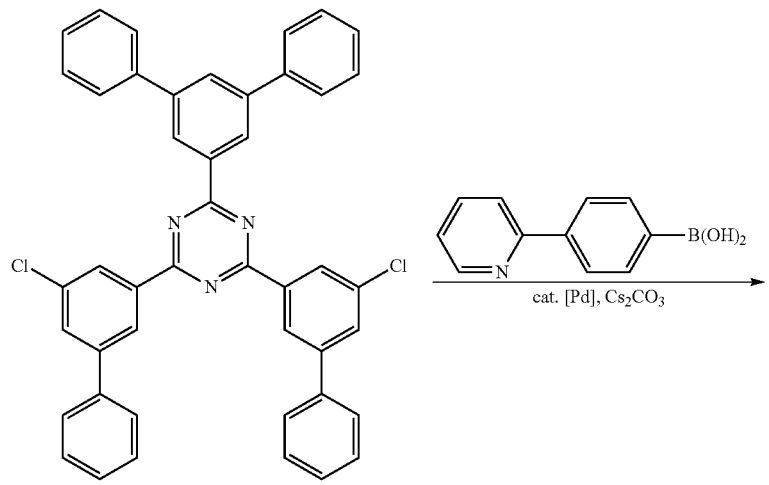

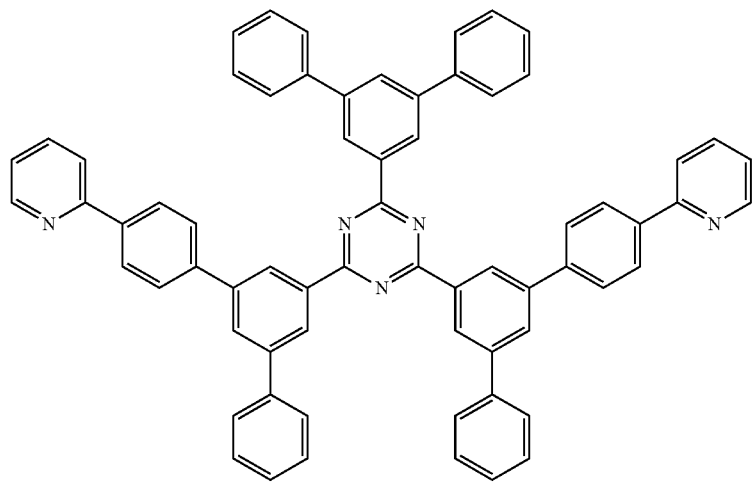

In a stream of argon, 4-(2-pyridyl)phenylboronic acid (1.19 g), 2,4-bis(5-chlrobiphenyl-3-yl)-6-(1,1':3',1''-terphenyl-5'-yl)-1,3,5-triazine (1.36 g), cesium carbonate (1.95 g), palladium acetate (17.9 mg) and 2-dicyclohexylphosphino-2',4',6'-triisopropylbiphenyl (75.9 mg) were suspended in tetrahydrofuran (160 ml), and the suspension was refluxed for 19 hours. The reaction mixture was left to stand at room temperature, and then low-boiling ingredients were distilled away under a reduced pressure. Methanol was added to the obtained solid. The solid precipitate was recovered by filtration, and the obtained crude product was purified by silica gel chromatography using a methanol/chloroform (0:100-1:66) mixed liquid as a developing solvent to give 890 mg of the target 2,4-bis[4-(2-pyridyl)-1,1':3',1''-terphenyl-5'-yl]-6-(1,1':3',1''-terphenyl-5'-yl)-1,3,5-triazine as a white powder (yield: 49%).

$^1$H-NMR (CDCl$_3$): δ7.27-7.32 (m, 2H), 7.44-7.50 (m, 4H), 7.53-7.60 (m, 8H), 7.78-7.87 (m, 12H), 7.94 (d, J=8.4 Hz, 4H), 8.09 (t, J=1.7 Hz, 1H), 8.14 (t, J=1.7 Hz, 2H), 8.19 (d, J=8.4 Hz, 4H), 8.78 (brddd, J=4.6, 1.3, 1.3 Hz, 2H), 9.03 (d, J=1.7 Hz, 2H), 9.05 (t, J=1.7 Hz, 2H), 9.08 (t, J=1.7 Hz, 2H).

Example 7

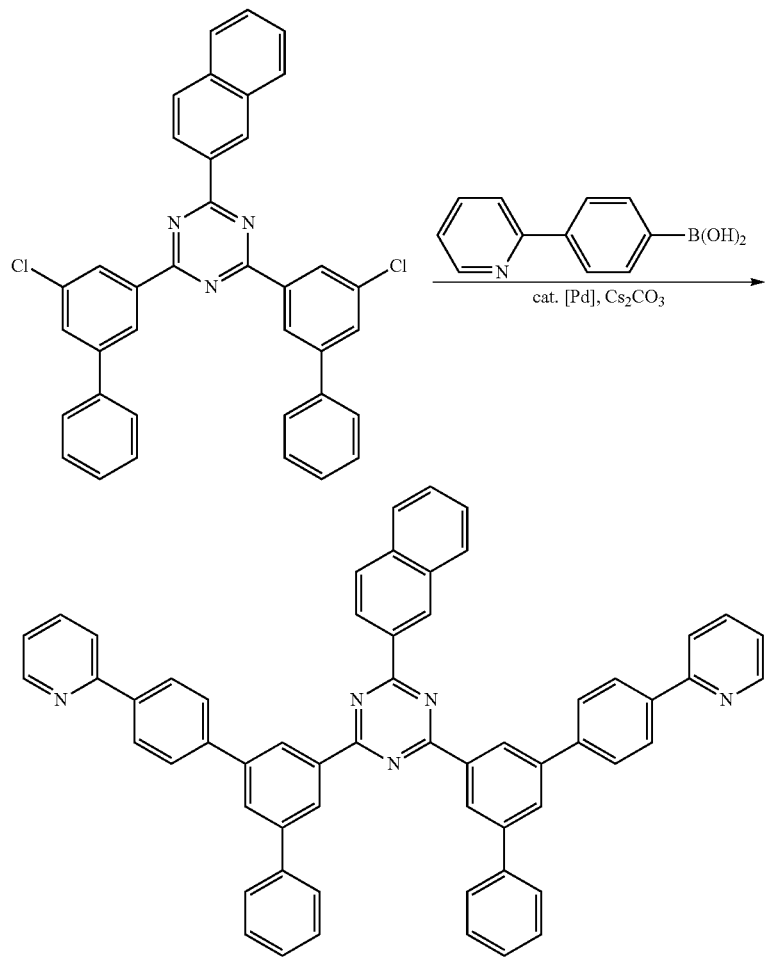

In a stream of argon, 4-(2-pyridyl)phenylboronic acid (2.06 g), 2,4-bis(5-chlrobiphenyl-3-yl)-6-(2-naphthyl)-1,3,5-triazine (2.00 g), cesium carbonate (3.68 g), palladium acetate (31.0 mg) and 2-dicyclohexylphosphino-2',4',6'-triisopropylbiphenyl (132 mg) were suspended in tetrahydrofuran (150 mL), and the suspension was refluxed for 22 hours. The reaction mixture was left to stand at room temperature, and then low-boiling ingredients were distilled away under a reduced pressure. Methanol was added to the obtained solid. The solid precipitate. was recovered by filtration, and the obtained crude product was purified by silica gel chromatography using a methanol/chloroform (1:100-1:66) mixed liquid as a developing solvent to give 2.67 g of the target 2-(2-naphthyl)-4,6-bis[4-(2-pyridyl)-1,1':3',1''-terphenyl-5'-yl]-1,3,5-triazine as a white powder (yield: 95%).

$^1$H-NMR (CDCl$_3$): δ7.26-7.33 (m, 2H), 7.49 (brt, J=7.3 Hz, 2H), 7.56-7.67 (m, 6H), 7.80-7.87 (m, 8H), 7.94-7.97 (m, 1H), 7.95 (d, J=8.4 Hz, 4H), 8.05 (d, J=8.7 Hz, 1H), 8.12 (t, J=1.6 Hz, 2H), 8.12-8.14 (m, 1H), 8.23 (d, J=8.4 Hz, 4H), 8.78 (brddd, J=4.6, 1.3, 1.3 Hz, 2H), 8.87 (dd, J=8.7, 1.6 Hz, 1H), 9.06 (t, J=1.6 Hz, 2H), 9.10 (t, J=1.6 Hz, 2H), 9.34 (brs, 1H).

$^{13}$C-NMR (CDCl$_3$): δ120.5 (CH×2), 122.2 (CH×2), 125.2 (CH), 126.4 (CH), 126.6 (CH×2), 126.9 (CH×2), 127.5 (CH×8), 127.7 (CH×4), 127.77 (CH×2), 127.84 (CH), 127.9 (CH), 128.4 (CH), 129.0 (CH×4), 129.7 (CH), 130.0 (CH×2), 130.2 (CH), 133.1 (quart.), 133.5 (quart.), 135.8 (quart.), 136.8 (CH×2), 137.4 (quart.×2), 138.8 (quart.×2), 140.8 (quart.×2), 141.3 (quart.×2), 141.6 (quart.×2), 142.4 (quart.×2), 149.8 (CH×2), 157.0 (quart.×2), 171.7 (quart.×2), 171.9 (quart.).

Example 8

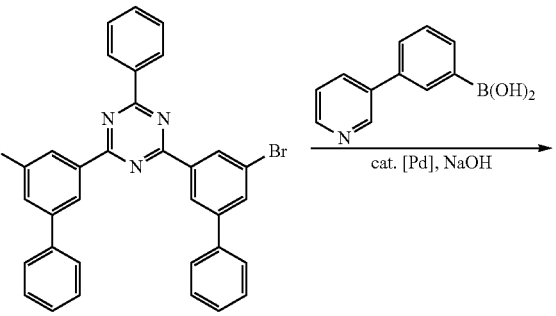

-continued

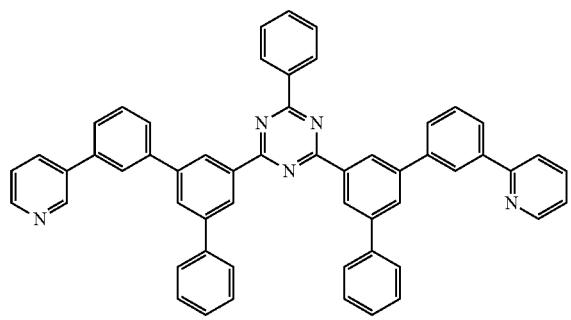

In a stream of argon, 3-(2-pyridyl)phenylboronic acid (149 mg), 2,4-bis(5-bromobiphenyl-3-yl)-6-phenyl-1,3,5-triazine (179.7 g), palladium acetate (1.4 mg) and a toluene solution (18.0 µL) of tri-tert-butylphosphine (1 mol/L) were suspended in tetrahydrofuran (5 mL). An aqueous solution (1.16 mL) of sodium hydroxide (4 mol/L) was dropwise added to the suspension over a period of 5 minutes. Then suspension was refluxed for 19 hours. The reaction mixture was left to stand at room temperature, and then low-boiling ingredients were distilled away under a reduced pressure. Methanol was added to the obtained solid. The solid precipitate was recovered by filtration. Thus, 200 mg of the target 6-phenyl-2,4-bis[3-(2-pyridyl)-1,1':3',1''-terphenyl-5'-yl]-1,3,5-triazine as a white powder (yield: 90%).

$^1$H-NMR (CDCl$_3$): δ7.33-7.39 (m, 2H), 7.44-7.48 (m, 2H), 7.53-7.57 (m, 4H), 7.61-7.69 (m, 5H), 7.85-7.93 (m, 10H), 8.12 (d, J=7.4 Hz, 2H), 8.19 (s, 2H), 8.45 (s, 2H), 8.78 (d, J=4.8 Hz, 2H), 8.86 (d, J=7.7 Hz, 2H), 9.06 (s, 2H), 9.09 (s, 2H).

Example 9

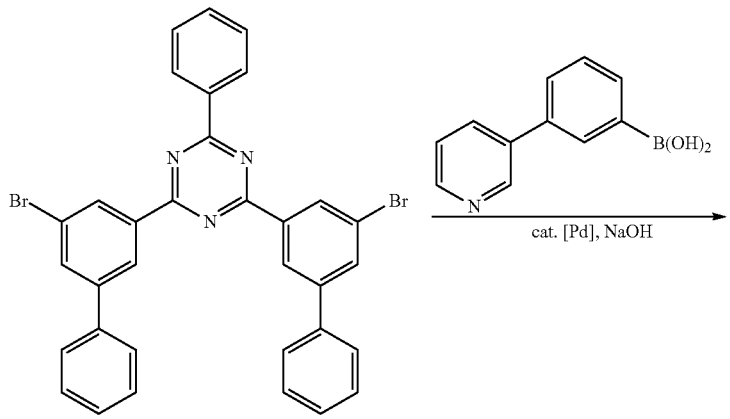

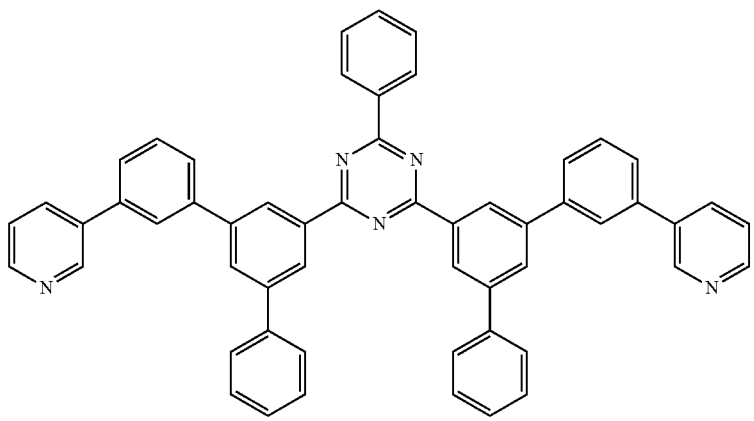

In a stream of argon, 3-(3-pyridyl)phenylboronic acid (1.04 g), 2,4-bis(5-bromobiphenyl-3-yl)-6-phenyl-1,3,5-triazine (1.24 g), palladium acetate (9.0 mg) and a toluene solution (120 μL) of tri-tert-butylphosphine (1 mol/L) were suspended in tetrahydrofuran (50 mL). An aqueous solution (2.0 mL) of sodium hydroxide (4 mol/L) was dropwise added to the suspension over a period of 5 minutes. Then suspension was refluxed for 19 hours. The reaction mixture was left to stand at room temperature, and then low-boiling ingredients were distilled away under a reduced pressure. Methanol was added to the obtained solid. The solid precipitate was recovered by filtration. Thus, 1.52 g of the target 6-phenyl-2,4-bis[3-(3-pyridyl)-1,1':3',1''-terphenyl-5'-yl]-1,3,5-triazine as a white powder (yield: 99%).

$^1$H-NMR (CDCl$_3$): δ7.29-7.49 (m, 4H), 7.54 (t, J=7.4 Hz, 4H), 7.60-7.68 (m, 7H), 7.80-7.84 (m, 6H), 7.96 (s, 2H), 8.03 (d, J=7.9 Hz, 2H), 8.07 (s, 2H), 8.67 (d, J=4.7 Hz, 2H), 8.81 (d, J=7.7 Hz, 2H), 8.99 (s, 2H), 9.02 (s, 4H).

$^{13}$C-NMR (CDCl$_3$): 6124.0, 125.8, 126.6, 126.7, 127.1, 127.5, 128.0, 128.8, 129.1, 129.2, 129.9, 130.4, 132.8, 135.2, 136.9, 137.5, 138.4, 140.6, 141.9, 141.9, 142.5, 147.9, 148.2, 171.7, 171.9.

Example 10

In a stream of argon, 6-phenylpyridin-3-ylboronic acid (1.29 g), 2,4-bis(5-bromobiphenyl-3-yl)-6-phenyl-1,3,5-triazine (1.55 g), palladium acetate (11.2 mg) and a toluene solution (150 μL) of tri-tert-butylphosphine (1 mol/L) were suspended in tetrahydrofuran (50 mL). An aqueous solution (4.7 mL) of sodium hydroxide (4 mol/L) was dropwise added to the suspension over a period of 5 minutes. Then suspension was refluxed for 19 hours. The reaction mixture was left to stand at room temperature, and then low-boiling ingredients were distilled away under a reduced pressure. The solid precipitate was recovered by filtration, and the obtained crude product was purified by silica gel chromatography using a hexane/chloroform (2:1-1:2) mixed liquid as a developing solvent, and then recrystallized from toluene to give 1.20 g of the target 2,4-bis[5-(6-phenylpyridin-3-yl)biphenyl-3-yl]-6-phenyl-1,3,5-triazine as a white powder (yield: 63%).

$^1$H-NMR (CDCl$_3$): δ7.49-7.69 (m, 15H), 7.84 (d, J=7.4 Hz, 4H), 7.96 (d, J=8.2 Hz, 2H), 8.10 (s, 2H), 8.14 (d, J=7.5 Hz, 4H), 8.23 (d, J=8.0 Hz, 2H), 8.84 (d, J=7.1 Hz, 2H), 9.04 (s, 2H), 9.07 (s, 2H), 9.19 (s, 2H).

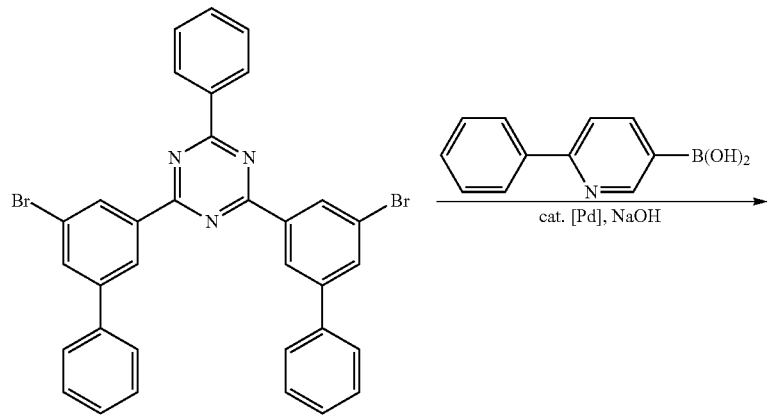

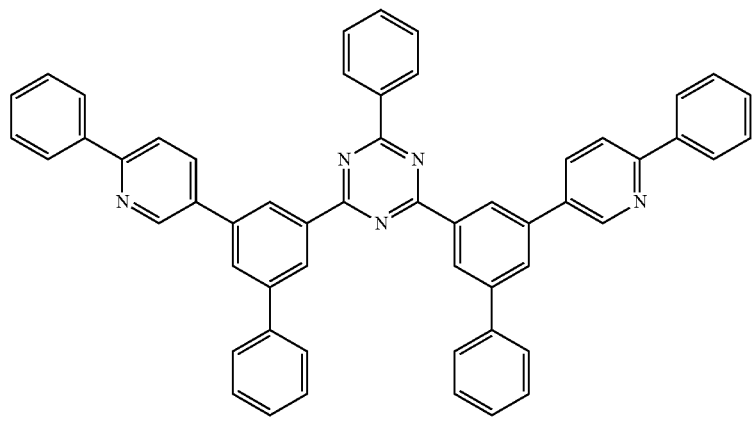

Example 11

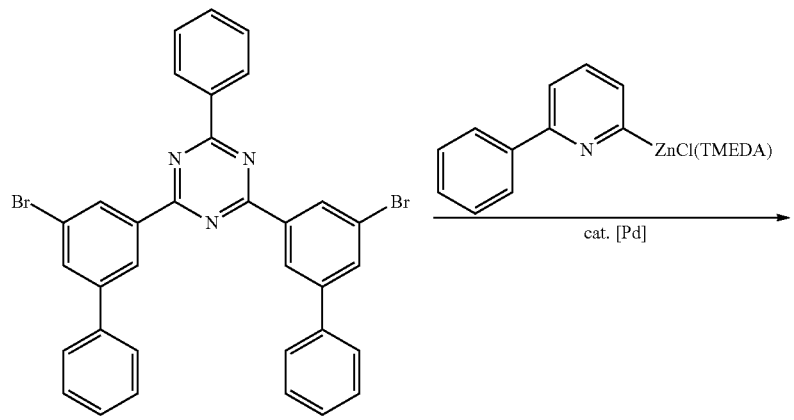

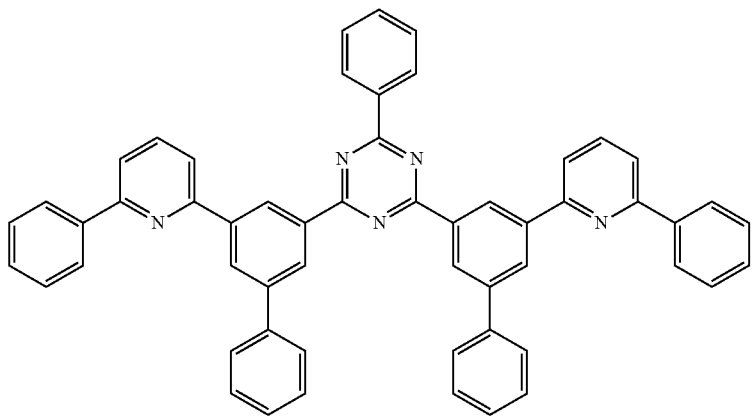

In a stream of argon, tetrahydrofuran (3 mL) was cooled to −78° C. To the cooled tetrahydrofuran, a tetrahydrofuran solution (1.18 mL) of tert-butyllithium (1.58 mol/L) was added. Then a tetrahydrofuran solution (2 mL) of 2-bromo-6-phenylpyridine (211 mg) was dropwise added to the tert-butyllithium solution. The mixture was stirred for 15 minutes while the mixture was maintained at −78° C. To the reaction mixture, zinc chloride tetramethylethylenediamine complex (530 mg) was added to allow the temperature to rise naturally to room temperature. Then, to the reaction mixture, a tetrahydrofuran suspension (2 mL) having suspended therein 2,4-bis(5-bromobiphenyl-3-yl)-6-phenyl-1,3,5-triazine (185.8 mg) and tetrakis(triphenylphosphine)palladium (13.9 mg) was dropwise added. The resultant mixture was stirred at 50° C. for 19 hours. The reaction mixture was left to stand at room temperature, and then low-boiling ingredients were distilled away under a reduced pressure. Methanol was added, and the solid precipitate was recovered by filtration. The obtained crude product was purified by silica gel chromatography using a hexane/chloroform (2:1) mixed liquid as a developing solvent, to give 120 mg of the target 2,4-bis[5-(6-phenylpyridin-2-yl)biphenyl-3-yl]-6-phenyl-1,3,5-triazine as a white powder (yield: 52%).

$^1$H-NMR (CDCl$_3$): δ7.29-7.60 (m, 15H), 7.82 (d, J=7.7 Hz, 2H), 7.91 (d, J=7.8H, 4H), 7.91 (t, J=7.7 Hz, 2H), 7.98 (d, J=7.7 Hz, 2H), 8.27 (d, J=7.2 Hz, 4H), 8.72 (s, 2H), 8.94 (d, J=6.4 Hz, 2H), 9.15 (s, 2H), 9.60 (s, 2H).

Example 12

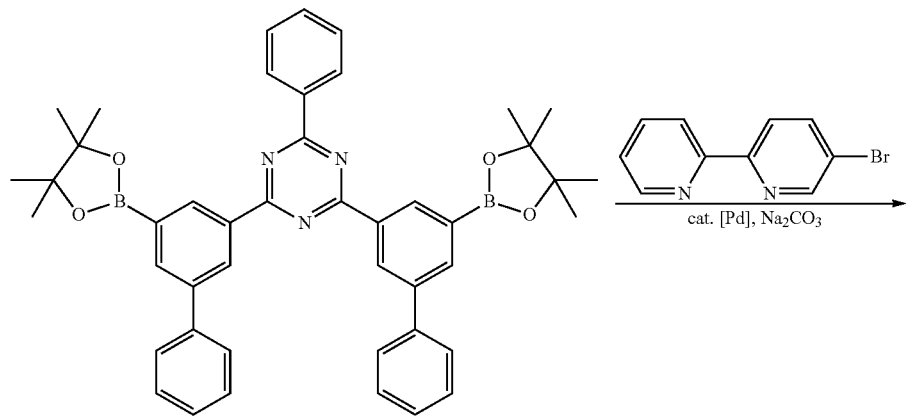

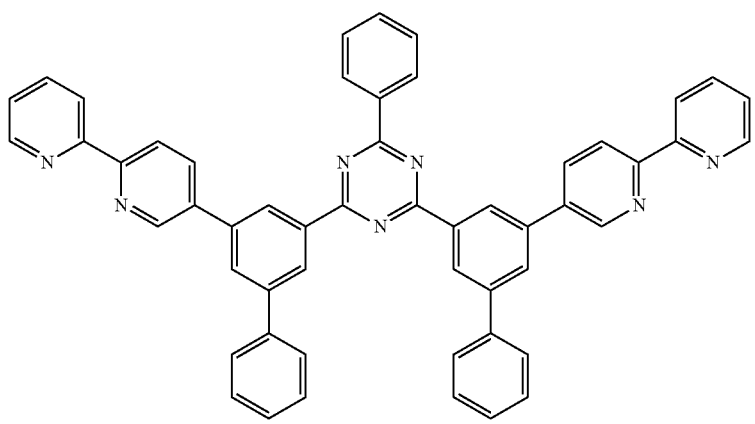

In a stream of argon, 2-phenyl-4,6-bis[5-(4,4,5,5-tetramethyl-1,3,2-dioxabororan-2-yl)biphenyl-3-yl]-1,3,5-triazine (1.50 g), 5-bromo-2,2'-bipyridine (1.23 g), tetrakis(triphenylphosphine)palladium (194 mg) and an aqueous 2M sodium carbonate solution (25 mL) were suspended in toluene (50 mL). The mixture was refluxed for 53 hours. The reaction mixture was left to stand at room temperature, and then low-boiling ingredients were distilled away under a reduced pressure. Water was added, and the solid precipitate was recovered by filtration. The obtained crude product was washed with methanol, and then, purified by silica gel chromatography using a methanol/chloroform (1:100-1:50) mixed liquid as a developing solvent, to give 1.32 g of the target 2,4-bis[5-(2,2'-bipyridin-5-yl)biphenyl-3-yl]-6-phenyl-1,3,5-triazine as a white powder (yield: 81%).

$^1$H-NMR (CDCl$_3$): δ7.39 (brt, J=5.7 Hz, 2H), 7.51 (t, J=7.2 Hz, 2H), 7.58-7.69 (m, 7H), 7.86 (d, J=7.3 Hz, 4H), 7.88-7.94 (m, 2H), 8.14 (t, J=1.8 Hz, 2H), 8.27 (dd, J=8.3, 2.3 Hz, 2H), 8.54 (d, J=8.0 Hz, 2H), 8.62 (d, J=8.5 Hz, 2H), 8.77 (brd, J=4.1 Hz, 2H), 8.87 (brd, J=7.8 Hz, 2H), 9.09 (t, J=1.8 Hz, 4H), 9.18 (d, J=1.8 Hz, 2H).

Example 13

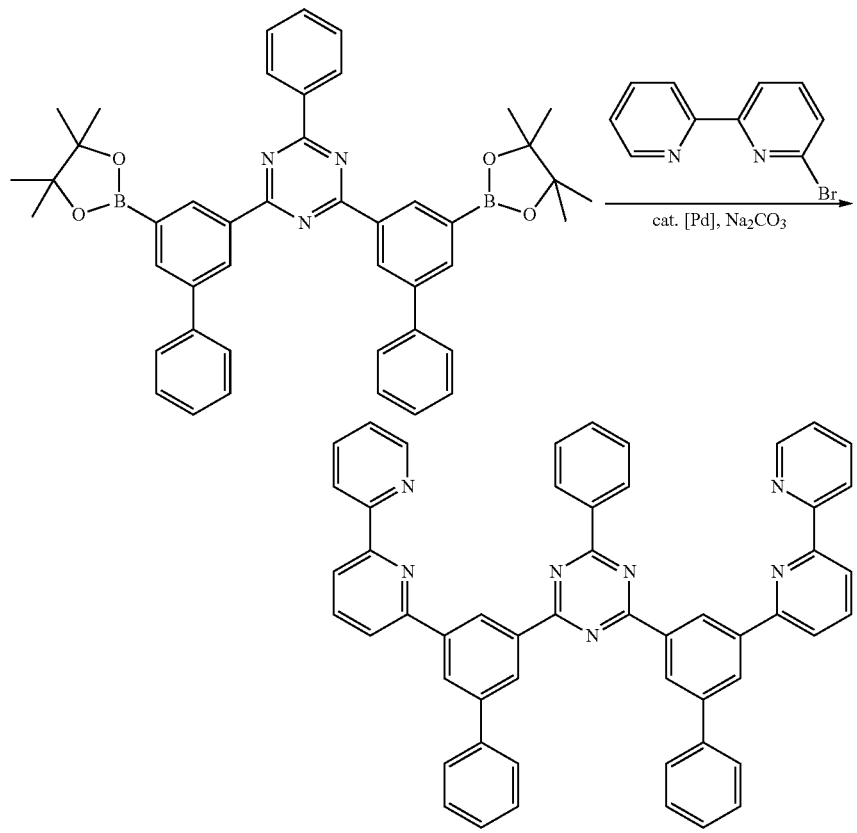

In a stream of argon, 2-phenyl-4,6-bis[5-(4,4,5,5-tetramethyl-1,3,2-dioxabororan-2-yl)biphenyl-3-yl]-1,3,5-triazine (1.17 g), 6-bromo-2,2'-bipyridine (925 mg), tetrakis(triphenylphosphine)palladium (152 mg) and an aqueous 2M sodium carbonate solution (20 mL) were suspended in toluene (50 mL). The mixture was refluxed for 72 hours. The reaction mixture was left to stand at room temperature, and then low-boiling ingredients were distilled away under a reduced pressure. Methanol was added, and the solid precipitate was recovered by filtration. The obtained crude product was washed with methanol and with water, and then, purified by silica gel chromatography using a methanol/chloroform (1:77-1:50) mixed liquid as a developing solvent, to give 976 mg of the target 2,4-bis[5-(2,2'-bipyridin-6-yl)biphenyl-3-yl]-6-phenyl-1,3,5-triazine as a white powder (yield: 77%).

$^1$H-NMR (CDCl$_3$): δ7.48-7.51 (m, 2H), 7.59 (t, J=7.8 Hz, 4H), 7.66-7.73 (m, 7H), 7.91 (brd, J=8.3 Hz, 4H), 7.97 (t, J=7.8 Hz, 2H), 8.06 (d, J=7.4 Hz, 2H), 8.49 (d, J=7.7 Hz, 2H), 8.70 (t, J=1.6 Hz, 2H), 8.73-8.75 (m, 2H), 8.76 (d, J=7.7 Hz, 2H), 8.94 (brd, J=4.2 Hz, 2H), 9.17 (t, J=1.6 Hz, 2H), 9.65 (t, J=1.6 Hz, 2H).

Device Example 1

Manufacture of an organic electroluminescent device comprising 1,3,5-triazine derivative as a constituent, and evaluation thereof A glass substrate with an indium-tin oxide (ITO) transparent electrode was prepared, which had a stripe pattern comprised of ITO film with a 2 mm width. The substrate was washed with isopropyl alcohol and then surface-treated by irradiation of ultraviolet rays and generation of ozone. Using the surface-treated substrate, an organic electroluminescent device with an emitting area of 4 mm$^2$ having a multilayer structure as illustrated in FIG. 1 was manufactured by forming each layer by vacuum deposition as follows.

The glass substrate was placed in a vacuum deposition chamber, and the inner pressure was reduced to 1.0×10$^{-4}$ Pa.

As illustrated in FIG. 1, on the above-mentioned glass substrate 1, organic compound layers, i.e., a hole injection layer 2, a hole transport layer 3, an emitting layer 4 and an electron transport layer 5 were formed in this order. Further a cathode layer 6 was formed. The hole injection layer 2 was formed by vacuum-depositing phthalocyanine copper(II), previously purified by sublimation, into a thickness of 25 nm. The hole transport layer 3 was formed by vacuum-depositing N,N'-di(naphthylen-1-yl)-N,N'-diphenylbenzidine (NPD) into a thickness of 45 nm.

The emitting layer 4 was formed by vacuum-depositing a mixture of 97 mass % of 4,4'-bis(2,2-diphenyl-ethen-1-yl)biphenyl (DPVBi) and 3 mass % of 4,4'-bis[4-(di-p-tolylamino)styryl]-biphenyl (DPAVBi) into a thickness of 40 nm. The electron transport layer 5 was formed by vacuum-depositing 6-phenyl-2,4-bis[4 (2-pyridyl)-1,1':3',1''-terphenyl-5'-yl]-1,3,5-triazine, synthesized in Example 1 according to the present invention, into a thickness of 20 nm.

The vacuum deposition of each organic material was conducted by subjecting each organic material to electric resistance heating to form a thin film at a deposition rate of from 0.3 to 0.5 nm/sec.

Then, a metal mask was arranged so as to be orthogonal to the ITO stripe, and a cathode layer 6 was vacuum-deposited.

The vacuum deposition of the cathode layer 6 was conducted so as to have a double layer structure comprising a lithium fluoride layer with a thickness of 0.5 nm and an aluminum layer with a thickness of 100 nm. The measurement of thickness of each organic material thin film layer was conducted by stylus profilometer ("DEKTAK").

Finally the thus-obtained assembly of multi-layers was encapsulated with a glass cap and ultraviolet ray-curable epoxy resin (available from Nagase Chemtex Corporation). The encapsulation was conducted in a nitrogen atmosphere having an oxygen-and-moisture content of below 1 ppm within a glove box.

Luminous properties of the thus-manufactured organic electroluminescent device were evaluated by applying a direct current using LUMINANCE METER BM-9 available from Topcon Corporation. The luminous properties as measured at a current density of 20 mA/cm$^2$ were as follows. Voltage 5.5 V, luminance 2240 cd/m$^2$, current efficiency 11.2 cd/A, power efficiency 6.3 lm/W. Luminance half-life of the device as measured at continuous lighting was 178 hours.

Device Example 2

By the same procedures as described in Device Example 1, an organic electroluminescent device was manufactured except that an emitting layer 4 was formed by vacuum-depositing tris(8-quinolinolato)aluminum (III) (Alq) into a thickness of 40 nm instead of the emitting layer formed from DPVBi/DPAVBi mixture in Device Example 1.

The thus-manufactured electroluminescent device exhibited a voltage of 4.6 V, a luminance of 953 cd/m$^2$, a current efficiency of 4.8 cd/A, and a power efficiency of 3.2 lm/W. Luminance half-life of the device was 3,510 hours.

Device Example 3

By substantially the same procedures as described in Device Example 1, an organic electroluminescent device as illustrated in FIG. 1 was manufactured and evaluated wherein the following hole injection layer 2, hole transport layer 3, emitting layer 4 and electron transport layer 5 were formed in this order on the glass substrate, and further the cathode layer 6 was formed. All other conditions and procedures remained the same.

The hole injection layer 2 was formed by vacuum-depositing phthalocyanine copper(II), previously purified by sublimation, into a thickness of 10 nm. The hole transport layer 3 was formed by vacuum-depositing N,N'-di(naphthylen-1-yl)-N,N'-diphenylbenzidine (NPD) into a thickness of 30 nm.

The emitting layer 4 was formed by vacuum-depositing a mixture of 94 mass % of 4,4'-bis(carbazol-9-yl)biphenyl (CBP) and 6 mass % of tris(2-phenylpyridine)iridium (III) [Ir(ppy)$_3$] into a thickness of 30 nm. The electron transport layer 5 was formed by vacuum-depositing 6-phenyl-2,4-bis[4-(2-pyridyl)-1,1':3',1''-terphenyl-5'-yl]-1,3,5-triazine, synthesized in Example 1 according to the present invention, into a thickness of 50 nm.

The thus-manufactured electroluminescent device exhibited a voltage of 10.1 V, a luminance of 2,690 cd/m$^2$, a current efficiency of 13.5 cd/A, and a power efficiency of 4.2 lm/W. Luminance half-life of the device was 105 hours.

Device Example 4

By the same procedures as described in Device Example 3, an organic electroluminescent device was manufactured and evaluated wherein the electron transport layer 5 was formed by vacuum-depositing 2-(2-naphthyl)-4,6-bis[4-(2-pyridyl)-1,1':3',1''-terphenyl-5'-yl]-1,3,5-triazine, synthesized in Example 7 according to the present invention, into a thickness of 50 nm. All other conditions and procedures remained the same.

The thus-manufactured electroluminescent device exhibited a voltage of 9.7 V, a luminance of 1,588 cd/m$^2$, a current efficiency of 7.9 cd/A, and a power efficiency of 2.6 lm/W. Luminance half-life of the device was 133 hours.

Device Example 5

By the same procedures as described in Device Example 3, an organic electroluminescent device was manufactured and evaluated wherein the electron transport layer 5 was formed by vacuum-depositing 2,4-bis[5-(2,2'-bipyridin-5-yl)biphenyl-3-yl]-6-phenyl-1,3,5-triazine, synthesized in Example 12 according to the present invention, into a thickness of 50 nm. All other conditions and procedures remained the same.

The thus-manufactured electroluminescent device exhibited a voltage of 9.1 V, a luminance of 2,070 cd/m$^2$, a current efficiency of 10.4 cd/A, and a power efficiency of 3.6 lm/W. Luminance half-life of the device was 131 hours.

Device Example 6

By the same procedures as described in Device Example 3, an organic electroluminescent device was manufactured and evaluated wherein the electron transport layer 5 was formed by vacuum-depositing 2,4-bis[5-(2,2'-bipyridin-6-yl)biphenyl-3-yl]-6-phenyl-1,3,5-triazine, synthesized in Example 13 according to the present invention, into a thickness of 50 nm. All other conditions and procedures remained the same.

The thus-manufactured electroluminescent device exhibited a voltage of 8.6 V, a luminance of 3,850 cd/m$^2$, a current efficiency of 19.3 cd/A, and a power efficiency of 7.1 lm/W. Luminance half-life of the device was 103 hours.

Comparative Device Example 1

By the same procedures as described in Device Example 1, an organic electroluminescent device was manufactured except that the electron transport layer 5 was formed by vacuum-depositing a conventional electron transport material, Alq, into a thickness of 20 nm. All other conditions and procedures remained the same.

The thus-manufactured electroluminescent device exhibited a voltage of 6.8 V, a luminance of 1,939 cd/m$^2$, a current efficiency of 9.7 cd/A, and a power efficiency of 4.5 lm/W. Luminance half-life of the device was 163 hours.

Comparative Device Example 2

By the same procedures as described in Device Example 2, an organic electroluminescent device was manufactured except that the electron transport layer 5 was formed by vacuum-depositing a conventional electron transport material, Alq, into a thickness of 20 nm. All other conditions and procedures remained the same.

The thus-manufactured electroluminescent device exhibited a voltage of 5.4 V, a luminance of 917 cd/m$^2$, a current efficiency of 4.6 cd/A, and a power efficiency of 2.7 lm/W. Luminance half-life of the device was 1,680 hours.

Comparative Device Example 3

By the same procedures as described in Device Example 3, an organic electroluminescent device was manufactured except that the electron transport layer 5 was formed by vacuum-depositing a conventional electron transport material, Alq, into a thickness of 50 nm. All other conditions and procedures remained the same.

The thus-manufactured electroluminescent device exhibited a voltage of 10.4 V, a luminance of 3,450 cd/m$^2$, a current efficiency of 17.3 cd/A, and a power efficiency of 5.2 lm/W. Luminance half-life of the device was 108 hours.

INDUSTRIAL APPLICABILITY

An organic electroluminescent device comprising as a constituent the 1,3,5-triazine derivative according to the present invention was proved to exhibit a low power consumption and a long lifetime as compared with the organic electroluminescent devices made of known materials. The compound of the present invention can be applied broadly to an electron transport layer of organic electroluminescent devices, as disclosed in the above examples, and to other layers including an luminescent host layer using luminescent materials, and fluorescent materials and phosphorescent materials. The organic electroluminescent device of the present invention can be applied broadly to fields including flat panel displays, and lighting equipments to which low power consumption and long lifetime are required.

The invention claimed is:

1. A 1,3,5-triazine compound represented by the following formula (1):

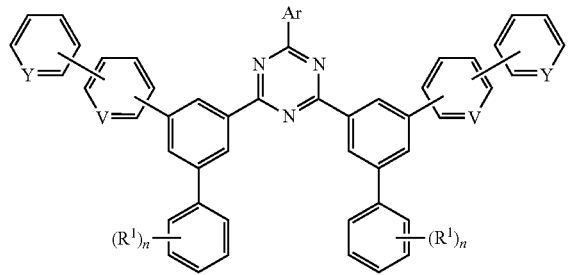

(1)

wherein:
R$^1$ represents a hydrogen atom, an alkyl group having 1 to 4 carbon atoms, or a substituted or unsubstituted phenyl group; n is an integer of 1 to 3, and, when n is 2 or 3, R$^1$ may be the same or different;
Ar represents an unsubstituted or methyl-substituted or phenyl-substituted or di-phenyl-substituted phenyl group, or a naphthyl group; and
V and Y independently represent a nitrogen atom or a carbon atom, provided that a case where both of V and Y are carbon atoms is excluded.

2. The 1,3,5-triazine compound according to claim 1, wherein R$^1$ represents a hydrogen atom, a methyl group or a phenyl group.

3. An organic electroluminescent device comprising as a constituent a 1,3,5-triazine compound represented by the following formula (1):

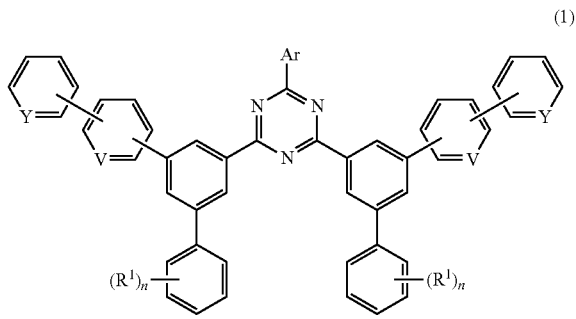

(1)

wherein:
R$^1$ represents a hydrogen atom, an alkyl group having 1 to 4 carbon atoms, or a substituted or unsubstituted phenyl group; n is an integer of 1 to 3, and, when n is 2 or 3, R$^1$ may be the same or different;
Ar represents an unsubstituted, methyl-substituted, phenyl-substituted, or di-phenyl-substituted phenyl group, or a naphthyl group; and
V and Y independently represent a nitrogen atom or a carbon atom, provided that a case where both of V and Y are carbon atoms is excluded.

* * * * *